US012788963B2

(12) United States Patent
Xie et al.

(10) Patent No.: US 12,788,963 B2
(45) Date of Patent: Nov. 10, 2026

(54) DRIVING DEVICE AND BLOOD PUMP

(71) Applicant: Shenzhen Core Medical Technology Co., Ltd., Shenzhen (CN)

(72) Inventors: Duanqing Xie, Shenzhen (CN); Shunzhou Yu, Shenzhen (CN)

(73) Assignee: Shenzhen Core Medical Technology Co., Ltd., Shenzhen (CN)

( * ) Notice: Subject to any disclaimer, the term of this patent is extended or adjusted under 35 U.S.C. 154(b) by 555 days.

(21) Appl. No.: 18/281,986

(22) PCT Filed: Nov. 15, 2022

(86) PCT No.: PCT/CN2022/132058
§ 371 (c)(1),
(2) Date: Sep. 14, 2023

(87) PCT Pub. No.: WO2023/098472
PCT Pub. Date: Jun. 8, 2023

(65) Prior Publication Data

US 2024/0299732 A1 Sep. 12, 2024

(30) Foreign Application Priority Data

Dec. 3, 2021 (CN) ......................... 202111479375.7

(51) Int. Cl.
*A61M 60/531* (2021.01)
*A61M 25/00* (2006.01)
(Continued)

(52) U.S. Cl.
CPC .......... *A61M 60/531* (2021.01); *A61M 60/13* (2021.01); *A61M 60/242* (2021.01);
(Continued)

(58) Field of Classification Search
None
See application file for complete search history.

(56) References Cited

U.S. PATENT DOCUMENTS 5,964,694 A * 10/1999 Siess .................... A61M 60/88 623/3.1
6,139,487 A 10/2000 Siess
(Continued)

FOREIGN PATENT DOCUMENTS

CN 1222863 A 7/1999
CN 109475671 A 3/2019
(Continued)

OTHER PUBLICATIONS

Office Action for Japanese Application No. 2023-561227 mailed Aug. 27, 2024. 6 pgs.
(Continued)

*Primary Examiner* — Mallika D Fairchild
(74) *Attorney, Agent, or Firm* — Lerner David LLP

(57) ABSTRACT

A driving device and a blood pump. The driving device comprises a driving housing, a shaft sleeve assembly, a rotating shaft, a driving component and a sensing assembly. An accommodating cavity and a detection port in communication with the accommodating cavity are provided on the shaft sleeve assembly, and the detection port is located on an outer wall of the shaft sleeve assembly; the rotating shaft is rotatably arranged on the shaft sleeve assembly; the driving component can drive the rotating shaft to rotate; and the sensing assembly comprises a sensor, the sensor comprising a probe, the probe being accommodated in the accommodating cavity, a position of the probe corresponding to a position of the detection port, and the probe being capable of detecting pressure of a fluid outside the driving device.

19 Claims, 16 Drawing Sheets

(51) Int. Cl.
*A61M 60/13* (2021.01)
*A61M 60/242* (2021.01)
*A61M 60/422* (2021.01)

(52) U.S. Cl.
CPC ... *A61M 60/422* (2021.01); *A61M 2025/0002* (2013.01); *A61M 2205/3306* (2013.01); *A61M 2205/3344* (2013.01)

(56) References Cited

U.S. PATENT DOCUMENTS

| | | | | |
|---|---|---|---|---|
| 6,234,772 | B1 | 5/2001 | Wampler et al. | |
| 7,011,620 | B1 | 3/2006 | Siess | |
| 2015/0141842 | A1 | 5/2015 | Spanier et al. | |
| 2017/0348470 | A1* | 12/2017 | D'Ambrosio | A61M 60/546 |
| 2018/0021497 | A1 | 1/2018 | Nunez et al. | |
| 2019/0255234 | A1 | 8/2019 | Menon et al. | |
| 2019/0282744 | A1 | 9/2019 | D'Ambrosio et al. | |
| 2020/0030510 | A1 | 1/2020 | Higgins | |
| 2020/0269025 | A1 | 8/2020 | Nitzan et al. | |
| 2021/0008261 | A1 | 1/2021 | Calomeni et al. | |

FOREIGN PATENT DOCUMENTS

| | | | |
|---|---|---|---|
| CN | 109843350 | A | 6/2019 |
| CN | 112472999 | A | 3/2021 |
| CN | 112494803 | A | 3/2021 |
| CN | 112533662 | A | 3/2021 |
| CN | 112569467 | A | 3/2021 |
| CN | 213100415 | U | 5/2021 |
| CN | 113476738 | A | 10/2021 |
| CN | 113476739 | A | 10/2021 |
| CN | 114870241 | A | 8/2022 |
| EP | 2841122 | B1 | 10/2015 |
| JP | 2000-512191 | A | 9/2000 |
| JP | 2002-541985 | A | 12/2002 |
| JP | 2019-523110 | A | 8/2019 |
| WO | 2021062270 | A1 | 4/2021 |

OTHER PUBLICATIONS

Search Report for Chinese Applicatio No. 2021114793757 dated Jul. 10, 2024. 3 pgs. (see p. 2, categorizing the cited references).

Extended European Search Report including Written Opinion for Application No. 22900277.9 dated Feb. 11, 2025, pp. 1-10.

International Search Report for PCT/CN2022/132058 mailed Jan. 20, 2023. 3 pgs.

* cited by examiner

DRIVING DEVICE AND BLOOD PUMP

CROSS REFERENCE TO RELATED APPLICATION

The present application is a US national stage disclosure of PCT international disclosure PCT/CN2022/132058, filed on Nov. 15, 2022, which claims priority to the Chinese Patent Application No. 202111479375.7, filed on Dec. 3, 2021 and titled "Driving Device and Blood Pump", the content of which is expressly incorporated herein by reference in its entirety.

TECHNICAL FIELD

The present disclosure relates to the field of medical device technology, and particularly to a drive device and a blood pump.

BACKGROUND

An intravascular blood pump is a device designed to be inserted percutaneously into a patient's blood vessel and probed into the patient's heart as a left ventricular assist device and/or a right ventricular assist device. The intravascular blood pump may also be referred to as an intracardiac blood pump. The current intravascular blood pump is usually delivered to a specific position through the blood vessel by means of a guide wire, and implements the auxiliary function thereof at the specific position. For this purpose, a sensor may be provided on the blood pump to detect the position of the blood pump. However, the provision of the sensor may increase the size of the blood pump.

SUMMARY

In view of this, the present disclosure provides a drive device and a blood pump which can detect the position of the blood pump more accurately and have a smaller size.

A drive device includes:

a drive housing;

a shaft sleeve assembly fixedly connected to the drive housing, wherein the shaft sleeve assembly is provided with a receiving cavity and a detection port communicated with the receiving cavity, and the detection port is located on an outer wall of the shaft sleeve assembly;

a rotating shaft, rotatably passing through the shaft sleeve assembly;

a drive component, mounted on the drive housing and capable of driving the rotating shaft to rotate; and a sensor assembly comprising a sensor, the sensor comprising a probe, wherein the probe is received in the receiving cavity, a position of the probe corresponds to a position of the detection port, and the probe is capable of detecting a fluid pressure outside the drive device.

A blood pump includes a rotatable impeller and the above-mentioned drive device.

The details of one or more embodiments of the present disclosure are set forth in the accompanying drawings and the description below. Other features, objects and advantages of the present disclosure will be obvious from the description, drawings and claims.

BRIEF DESCRIPTION OF THE DRAWINGS

In order to illustrate the technical solution of the embodiments of the present disclosure more clearly, the accompanying drawings used in the description of the embodiments of the present disclosure or in the description of the existing technology will be briefly introduced below. Obviously, the accompanying drawings in the following description are merely some embodiments of the present disclosure, and those skilled in the art can also obtain other drawings according to these drawings without any creative effort.

DETAILED DESCRIPTION

In order to make the purpose, the technical solution and advantages of the present disclosure clearer, the present disclosure will be further described in detail below in conjunction with the accompanying drawings, i.e., embodiments. It should be appreciated that the specific embodiments described here are merely used for explaining the present disclosure, not to limit the present disclosure.

It should be noted that when an element is referred to as being "fixed to" or "provided on" another element, the element may be directly or indirectly on the other element. When an element is referred to as being "connected to" another element, the element may be directly or indirectly connected to the other element.

In addition, the terms "first", "second" are used for descriptive purposes only, and cannot be interpreted as indicating or implying relative importance or implicitly specifying the quantity of indicated technical features. Thus, a feature defined as "first", "second" may explicitly or implicitly include one or more of these features. In the description of the present disclosure, "plurality" means two or more, unless otherwise specifically defined.

In order to illustrate the technical solution of the present disclosure, the illustration below will be provided in conjunction with specific drawings and embodiments.

Figure 1:
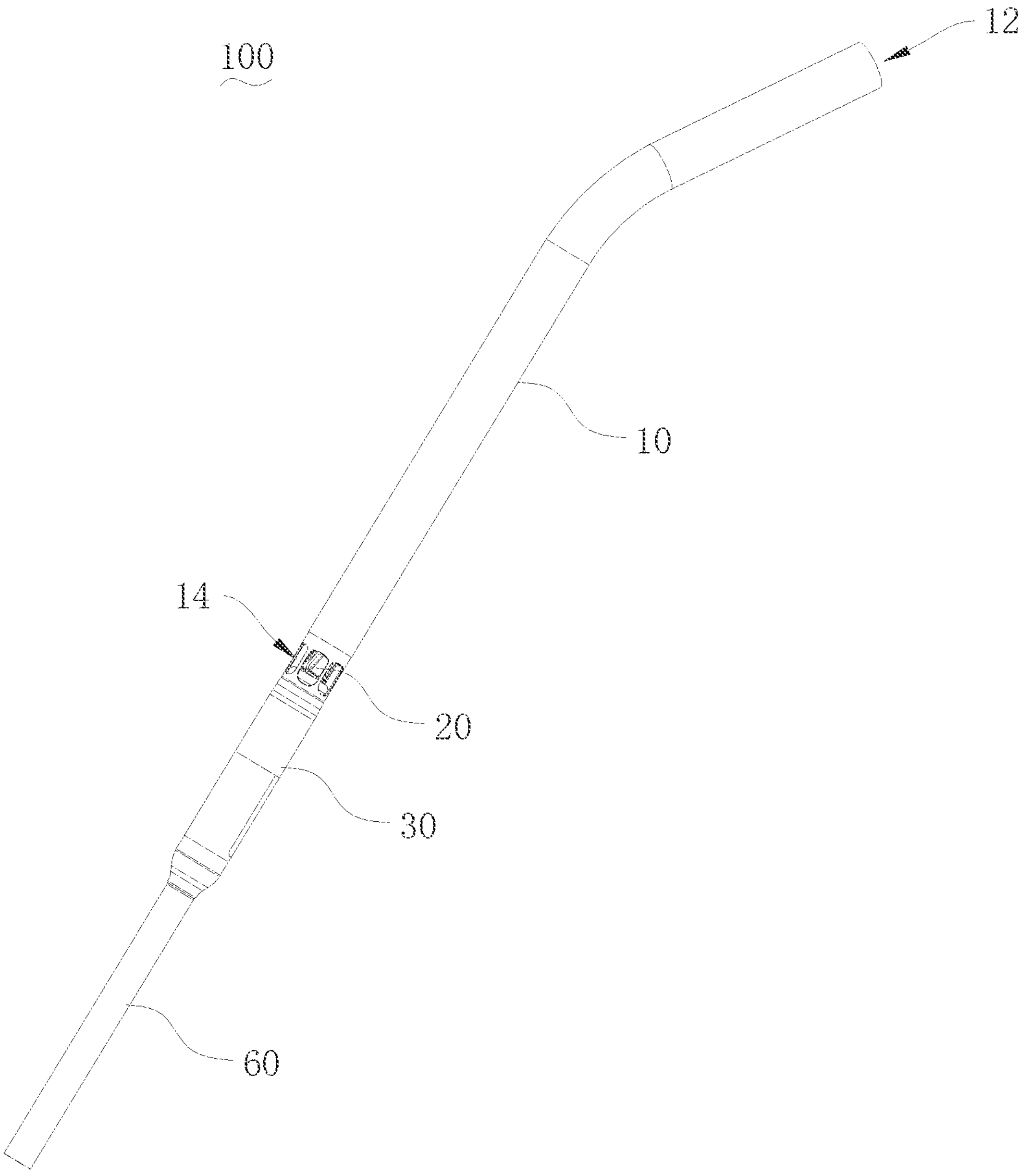
FIG. 1 is a schematic structure diagram of a blood pump according to an embodiment I.
Figure 2:
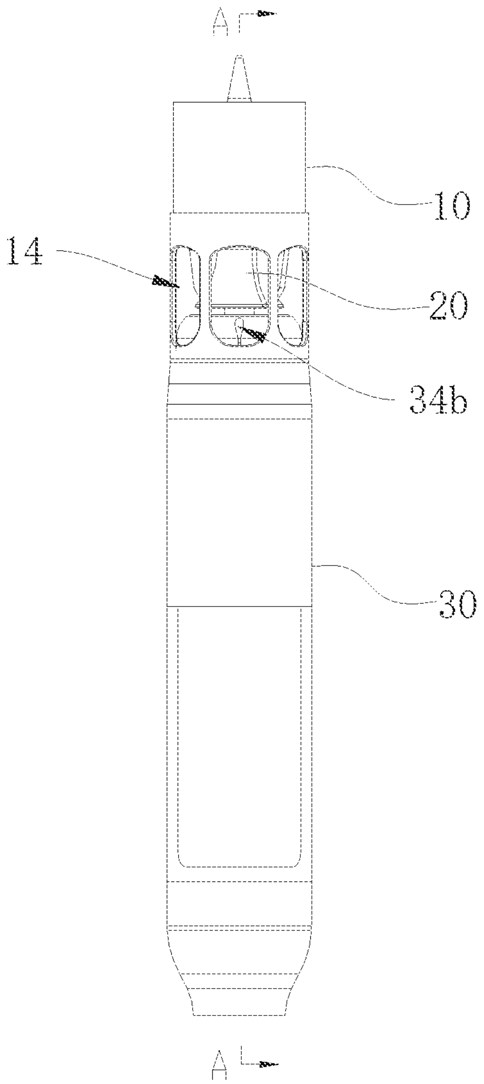
FIG. 2 is a schematic structure diagram of the blood pump shown in FIG. 1 omitting a catheter assembly and a partial cannula assembly.
Figure 3:
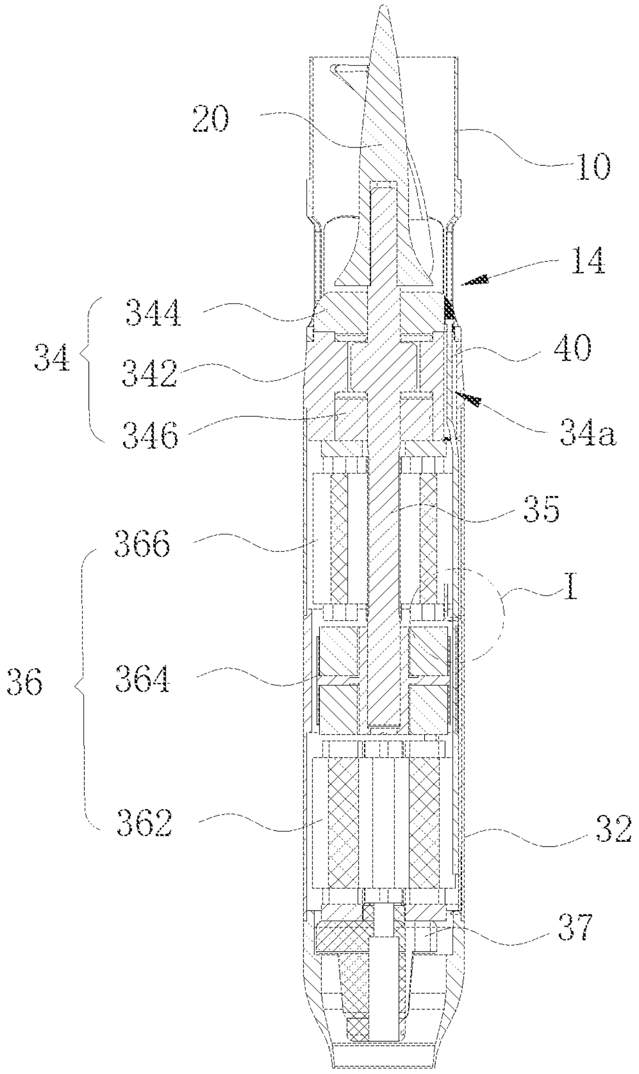
FIG. 3 is a section view of FIG. 2 along A-A.

As shown in FIGS. 1 to 3, a blood pump 100 in the first implementation mode specifically relates to an intravascular blood pump. The blood pump 100 includes a cannula assembly 10, an impeller 20 and a drive device 30.

The cannula assembly 10 is provided with an inflow port 12 and an outflow port 14. In an embodiment, in use, the cannula assembly 10 extends through a heart valve, such as an aortic valve; the inflow port 12 is located within the heart and the outflow port 14 is located outside the heart, such as in a blood vessel of the aorta. Specifically, in the illustrated embodiment, the inflow port 12 and the outflow port 14 are respectively provided adjacent to two ends of the cannula assembly 10.

The impeller 20 is rotatably received in the cannula assembly 10. When the impeller 20 rotates, blood flows into the cannula assembly 10 from the inflow port 12 of the cannula assembly 10, and then flows out of the cannula assembly 10 through the outflow port 14. In the illustrated embodiment, the impeller 20 is provided at one end of the cannula assembly 10 adjacent to the outflow port 14.

The drive device 30 is fixedly connected to the cannula assembly 10. Specifically, the drive device 30 is fixedly connected to an end of the cannula assembly 10 adjacent to the outflow port 14. The drive device 30 is in transmission connection with the impeller 20, and the drive device 30 is capable of driving the impeller 20 to rotate.

In the embodiment, the drive device 30 includes a drive housing 32, a shaft sleeve assembly 34, a rotating shaft 35, a drive component 36 and a sensor assembly 40.

The drive housing 32 generally has a tubular structure. The drive housing 32 has two opposing open ends.

The bushing assembly 34 is fixedly connected to the driving housing 32. Specifically, the shaft sleeve assembly 34 is affixed to one end of the drive housing 32, and the shaft sleeve assembly 34 is sealed with the drive housing 32; the cannula assembly 10 is fixedly connected to the shaft sleeve assembly 34. In the illustrated embodiment, the shaft sleeve assembly 34 is located between the cannula assembly 10 and the drive housing 32. It can be understood that, in other embodiments, the cannula assembly 10 may also be fixed directly to the drive housing 32, and at the moment the shaft sleeve assembly 34 is at least partially received in the cannula assembly 10.

Figure 4:
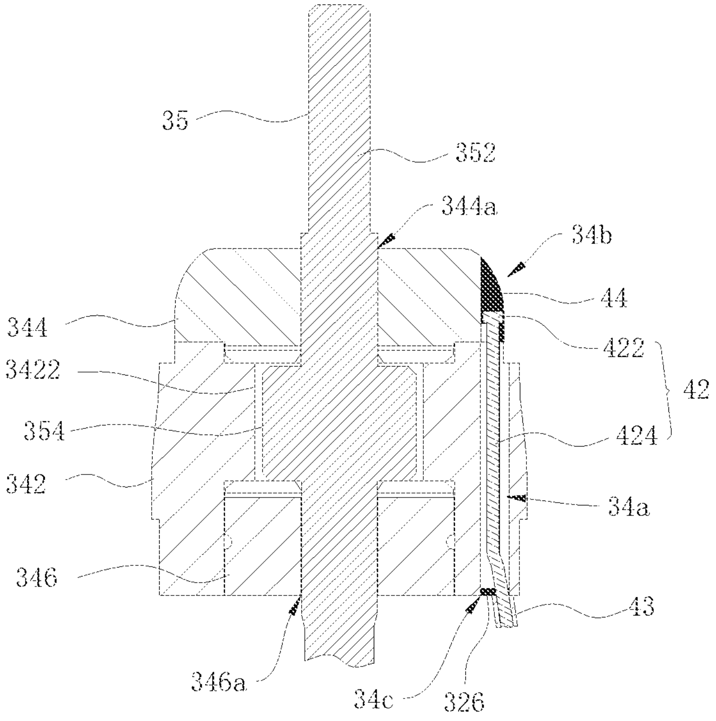
FIG. 4 is a partial section view of a blood pump omitting a cannula assembly, an impeller, a drive component, a drive housing, part of a rotating shaft and part of a sensor assembly according to an embodiment (the sensor assembly in the embodiment of FIG. 4 has a packaging tube).
Figure 5:
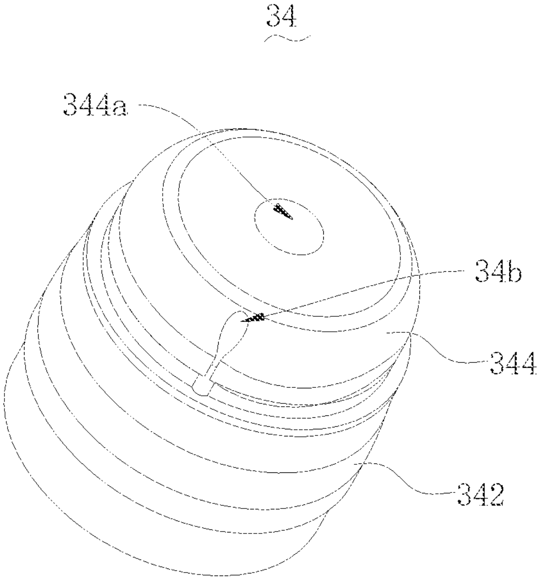
FIG. 5 is a three-dimensional schematic diagram of a shaft sleeve assembly of the blood pump shown in FIG. 1.

Referring to FIG. 4, the shaft sleeve assembly 34 is provided with a receiving cavity 34*a* and a detection port 34*b* communicating with the receiving cavity 34*a*, and the detection port 34*b* is located on an outer wall of the shaft sleeve assembly 34. Specifically, the detection port 34*b* is an opening of the receiving cavity 34*a*. In the present disclosure, the outer wall of the shaft sleeve assembly 34 includes an outer peripheral wall of the shaft sleeve assembly 34 and outer end surfaces of both axial ends of the shaft sleeve assembly 34. In other words, the detection port 34*b* may be located on the outer peripheral wall of the shaft sleeve assembly 34, or may be located on the outer end surfaces of both ends of the shaft sleeve assembly 34, or may be partially located on the outer peripheral wall of the shaft sleeve assembly 34, and partially located on the outer end surface.

Specifically, the position of the detection port 34*b* is adjacent to the outflow port 14, or the position of the detection port 34*b* corresponds to the position of the outflow port 14. In the illustrated embodiment, the position of the detection port 34*b* corresponds to the position of the outflow port 14. Specifically, the shaft sleeve assembly 34 is partially received in the cannula assembly 10, and the detection port 34*b* is located on a portion of the shaft sleeve assembly 34 received in the cannula assembly 10, and is opposite to the outflow port 14.

The rotating shaft 35 can rotatably pass through the shaft sleeve assembly 34; one end of the rotating shaft 35 extends into the drive housing 32, and the other end extends away from the drive housing 32 and is fixedly connected to the impeller 20. Specifically, an end of the rotating shaft 35 away from the drive housing 32 extends into the cannula assembly 10 and is fixedly connected to the impeller 20. The rotating shaft 35 and the shaft sleeve assembly 34 together form a bearing structure.

In the embodiment, the shaft sleeve assembly 34 includes an adapter sleeve 342 and a first shaft sleeve 344; the adapter sleeve 342 is fixedly connected to the drive housing 32, the first shaft sleeve 344 is fixedly connected to the adapter sleeve 342, and the rotating shaft 35 can be rotatably passed through the first shaft sleeve 344 and the adapter sleeve 342. Specifically, the first shaft sleeve 344 is provided with a first shaft hole 344*a*, and the first shaft hole 344*a* is communicated with the adapter sleeve 342, and the rotating shaft 35 can be rotatably passed through the first shaft hole 344*a* and the adapter sleeve 342. The first shaft sleeve 344 and the rotating shaft 35 together form a first bearing. At least one of the adapter sleeve 342 and the first shaft sleeve 344 is fixedly connected to the cannula assembly 10.

Specifically, the receiving cavity 34*a* is at least partially located in the first shaft sleeve 344, and the detection port 34*b* is at least partially located on the first shaft sleeve 344, or both the receiving cavity 34*a* and the detection port 34*b* are located on the adapter sleeve 342. In the illustrated embodiment, the receiving cavity 34*a* extends from the adapter sleeve 342 to the first shaft sleeve 344, and the detection port 34*b* is located on the first shaft sleeve 344. The first shaft hole 344*a* is spaced apart from the receiving cavity 34*a*.

In the illustrated embodiment, both ends of the adapter sleeve 342 are open. The first shaft sleeve 344 and the drive housing 32 are fixedly connected to both the open ends of the adapter sleeve 342 respectively, and the first shaft sleeve 344 is communicated with the adapter sleeve 342, the drive housing 32 communicates with the adapter sleeve 342. Specifically, an end of the adapter sleeve 342 away from the first shaft sleeve 344 is received in the drive housing 32.

Referring to FIGS. 5 to 8, in the illustrated embodiments, the first shaft sleeve 344 includes a disc-shaped cap portion 3442 and a convex plate 3444. The cap portion 3442 has a first surface and a second surface facing away from each other. The convex plate 3444 is formed on the first surface of the cap portion 3442. The cap portion 3442 is sealed over the opening of one end of the adapter sleeve 342 away from the drive housing 32. The first shaft hole 344*a* extends from an end surface of the convex plate 3444 away from the cap portion 3442 to the second surface of the cap portion 3442. The receiving cavity 34*a* extends from an end surface of the adapter sleeve 342 away from the cap portion 3442 onto the cap portion 3442, and the detection port 34*b* is located on the cap portion 3442. Specifically, an end of the convex plate 3444 away from the cap portion 3442 is received in the adapter sleeve 342. An end of the adapter sleeve 342 away from the cap portion 3442 is received in the drive housing 32.

Further, the shaft sleeve assembly 34 further includes a second shaft sleeve 346, the second shaft sleeve 346 is fixedly connected to the adapter sleeve 342, the second shaft sleeve 346 and the first shaft sleeve 344 are arranged along an axis of the rotating shaft 35. The first shaft sleeve 344 is more adjacent to the impeller 20 than the second shaft sleeve 346. The rotating shaft 35 is rotatably passed through the second shaft sleeve 346. The second shaft sleeve 346 and the rotating shaft 35 together form a second bearing. Adding the second shaft sleeve 346 based on the first shaft sleeve 344 can improve the rotation stability of the rotating shaft 35. Specifically, the second shaft sleeve 346 is provided with a second shaft hole 346*a*, and the rotating shaft 35 can be rotatably passed through the second shaft hole 346*a*. The second shaft sleeve 346 is received in the adapter sleeve 342.

Specifically, the second shaft sleeve 346 is fixed to the adapter sleeve 342 by an adhesive. In the illustrated embodiment, in order to fix and mount the second shaft sleeve 346 in the adapter sleeve 342 conveniently, the outer peripheral wall of the second shaft sleeve 346 is provided with an adhesive groove 346*b* configured to receive the adhesive.

In an embodiment, materials of the first shaft sleeve 344, the second shaft sleeve 346 and the rotating shaft 35 are ceramics, which are more corrosion-resistant, and have a longer service life, and are lighter in weight. It can be understood that, in other embodiments, the materials of the first shaft sleeve 344, the second shaft sleeve 346 and the rotating shaft 35 can also be metals; alternatively, part of the materials of the first shaft sleeve 344, the second shaft sleeve 346 and the rotating shaft 35 is ceramic, and the other part is metal; alternatively, the materials of the first shaft sleeve 344, the second shaft sleeve 346 and the rotating shaft 35 can also be other biocompatible materials.

Referring to FIG. 4 again, in the embodiment, the rotating shaft 35 includes a shaft body 352 and a convex ring 354 arranged around the shaft body 352. The shaft body 352 is rotatably passed through the first shaft hole 344*a*, the second shaft hole 346*a* and the adapter sleeve 342. One end of the shaft body 352 extends into the drive housing 32, and the other end extends away from the drive housing 32 and is connected to the impeller 20. The convex ring 354 is located between the first shaft sleeve 344 and the second shaft sleeve 346. An outer diameter of the convex ring 354 is greater than a hole diameter of the first shaft hole 344*a*, and is greater than a hole diameter of the second shaft hole 346*a*, in order to limit the rotating shaft 35 in the extension direction of the rotation shaft 35, and prevent the rotating shaft 35 from moving greatly with respect to the shaft sleeve assembly 34 in the extension direction of the rotating shaft 35. Specifically, an end of the shaft body 352 away from the drive housing 32 extends into the cannula assembly 10 and is fixedly connected to the impeller 20.

In the embodiment, a protrusion 3422 is provided on an inner wall of the adapter sleeve 342, and the protrusion 3422 is arranged around the axis of the rotating shaft 35 for one circle. The protrusion 3422 is positioned between the first shaft sleeve 344 and the second shaft sleeve 345; a position of the protrusion 3422 corresponds to a position of a protruding ring 354, and there is a gap between the protruding ring 354 and the protrusion 3422.

It should be noted that the shaft sleeve assembly 34 is not limited to the above-mentioned structure. In other embodiments, the second shaft sleeve 346 of the shaft sleeve assembly 34 may also be fixed within the drive housing 32, or the second shaft sleeve 346 of the shaft sleeve assembly 34 is partially received in the adapter sleeve 342 and partially received in the drive housing 32, or the second shaft sleeve 346 may not be provided. Alternatively, the shaft sleeve assembly 34 may also have the structure of the shaft sleeve assembly shown in FIGS. 17 to 20 or the structure of the shaft sleeve assembly shown in FIGS. 23 to 26.

Figure 9:
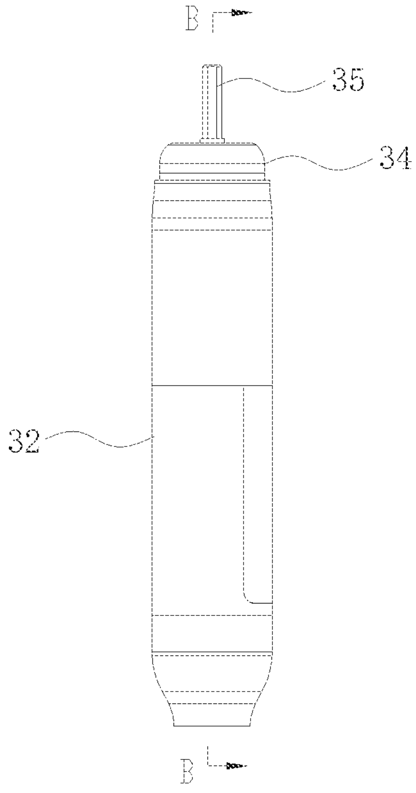
FIG. 9 is a schematic structure diagram of the drive device of the blood pump shown in FIG. 2 from another perspective.
Figure 10:
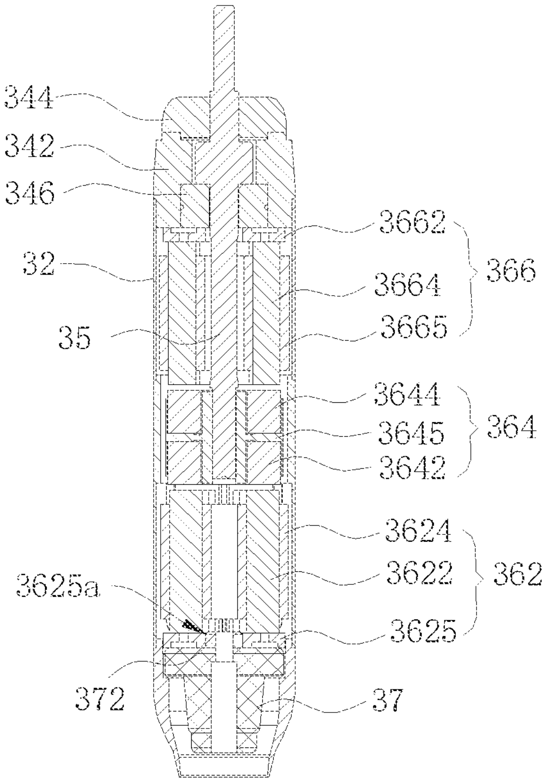
FIG. 10 is a section view of FIG. 9 along B-B.

Referring to FIG. 3, FIG. 9 and FIG. 10. The drive component 36 is mounted within the drive housing 32, and the drive component 36 can drive the rotating shaft 35 to rotate. The impeller 20 can rotate with the rotating shaft 35.

Specifically, the drive component 36 includes a drive stator 362 and a magnetic assembly 364; the drive stator 362 is fixed to the drive housing 32; the magnetic assembly 364 includes a first magnet 3642; the first magnet 3642 is fixed to the rotating shaft 35; and the drive stator 362 can generate a rotating magnetic field driving the first magnet 3642 to rotate around the axis of the rotating shaft 35, and the rotating shaft 35 can rotate with the first magnet 3642. In the illustrated embodiment, the magnetic assembly 364 is received within the drive housing 32.

Specifically, the drive stator 362 includes a plurality of first magnetic cores 3622 and a plurality of first coils 3624 respectively wound around the first magnetic cores 3622. The plurality of first magnetic cores 3622 are arranged at intervals around the axis of the rotating shaft 35. Specifically, an extension direction of each first magnetic core 3622 is parallel to the axis of the rotating shaft 35. The first coil 3624 can generate a rotating magnetic field that drives the first magnet 3642 to rotate, to drive the rotating shaft 35 to rotate, thereby driving the impeller 20 to rotate.

In the embodiment, the drive stator 362 and the rotating shaft 35 are spaced along the axis of the rotating shaft 35, that is, the rotating shaft 35 is not inserted into the drive stator 362. By spacing the drive stator 362 and the rotating shaft 35 in the axial direction, it is beneficial to set that the larger the cross-section of the magnetic core of the drive stator 362, the greater the cross-sectional area of the magnetic core, the greater the magnetic flux generated by the drive stator 362, the greater the torque to the first magnet 3642, and then the current required by the drive stator 362 to drive the rotating shaft 35 to rotate is correspondingly reduced, which is beneficial to reduce the power consumption and heat generation of the whole blood pump 100. Therefore, the blood pump 100 of the above-mentioned drive device 30 can have lower power consumption and less heat generation.

In the embodiment, the drive stator 362 further includes a first back plate 3625, and the first back plate 3625 is fixed to the drive housing 32. One end of each first magnetic core 3622 is fixed to the first back plate 3625, and the other end is extended to close to the first magnet 3642. The first back plate 3625 serves as a closed magnetic circuit to promote and increase the generation of the magnetic flux of the drive stator 362 to improve the coupling capability. Since the first back plate 3625 can increase the magnetic flux, the arrangement of the first back plate 3625 is beneficial to reduce the overall diameter of the blood pump 100.

Specifically, the first back plate 3625 is made of the same material as the first magnetic core 3622; and in some embodiments, both the first back plate 3625 and the first magnetic core 3622 are made of soft magnetic materials, such as cobalt steel.

In the embodiment, the drive device 30 further includes a fixing member 37 fixed within the drive housing 32, and a positioning column 372 is provided on the fixing member 37. A positioning hole 3625*a* is provided on the first back plate 3625, and the positioning column 372 passes through the positioning hole 3625*a*, to facilitate the positioning and mounting of the drive stator 362. The axis of the positioning column 372 coincides with the axis of the rotating shaft 35.

It should be noted that, in some embodiments, the drive stator 362 may not be provided with the first back plate 3625.

Specifically, the drive component 36 may further include a power stator 366 fixed to the drive housing 32. The power stator 366 and the drive stator 362 are arranged along the axis of the rotating shaft 35. The power stator 366 is more adjacent to the impeller 20 than the drive stator 362. The rotating shaft 35 is capable of rotatably passing through the power stator 366. The magnetic assembly 364 may further include a second magnet 3644 fixedly connected to the rotating shaft 35. The power stator 366 is capable of generating a rotating magnetic field that drives the second magnet 3644 to rotate. That is, the drive stator 362 and the power stator 366 can respectively drive the first magnet 3642 and the second magnet 3644 to rotate, so that the drive stator 362 and the power stator 366 can jointly drive the rotating shaft 35 to rotate around the axis of the rotating shaft 35, thereby driving the impeller 20 to rotate, in order to provide a greater driving force for the rotation of the impeller 20. Specifically, the first magnet 3642 is located between the drive stator 362 and the power stator 366, so that the drive stator 362 interacts with the first magnet 3642 to generate the rotating magnetic field that drives the first magnet 3642 to rotate.

In the illustrated embodiment, the power stator 366 is similar in structure to the drive stator 362. The power stator 366 includes a second back plate 3662, a plurality of second magnetic cores 3664, and a second coil 3665. The second back plate 3662 is fixed to at least one of the drive housing 32 and the shaft sleeve assembly 34. The plurality of second magnetic cores 3664 are arranged at intervals around the rotating shaft 35 for one circle. Specifically, an extension direction of each second magnetic core 3664 is parallel to the axis of the rotating shaft 35. One end of each second magnetic core 3664 is fixedly connected to the second back plane 3662, and the other end is extended to approximate to the second magnet 3644. Each second coil 3665 is respectively wound on a corresponding second magnetic core 3664. The second coil 3665 can generate a rotating magnetic field that drives the second magnet 3644 to rotate. It should be appreciated that the power stator 366 may be not provided with the second back plate 3662.

Specifically, both the first magnetic core 3622 and the second magnetic core 3664 include a magnetic pillar. The first coil 3624 is wound on a magnetic pillar of the first magnetic core 3622, the second coil 3665 is wound on a magnetic pillar of the second magnetic core 3664. A cross-sectional area of the magnetic pillar of the first magnetic core 3622 is greater than a cross-sectional area of the magnetic pillar of the second magnetic core 3664.

The greater the cross-sectional area of the magnetic pillar, the greater the magnetic flux generated, the greater the torque to the magnet, and the smaller the required current, which is beneficial to reduce power consumption and heat generation. Since the rotating shaft 35 passes through a middle portion of the power stator 366, the cross-sectional area of the second magnetic core 3664 is limited due to the limitation of a radial dimension of the blood pump 100; when the rotating shaft 35 does not pass through a middle portion of the drive stator 362, so that the first magnetic core 3622 can have a greater cross-sectional area. In other words, such an arrangement can reduce the power consumption and the heat generation of the drive device 30.

In the embodiment, both the first magnetic core 3622 and the second magnetic core 3664 have only magnetic pillars, that is, neither the first magnetic core 3622 nor the second magnetic core 3664 has a head portion (that is, a pole shoe) with a larger width. In a length direction of the first magnetic core 3622 and the second magnetic core 3664, the widths of the first magnetic core 3622 and the second magnetic core 3664 are constant, the entire first magnetic core 3622 can be magnetically coupled with the first magnet 3642, and the entire second magnetic core 3664 can be magnetically coupled with the second magnet 3644. Compared to a magnetic core provided with the pole shoe, the magnetic core in the present disclosure which is a magnetic pillar can reduce the magnetic loss, increase magnetic coupling densities between the first magnetic core 3622 and the first magnet 3642, and between the second magnetic core 3664 and the second magnet 3644123, to increase the torque of the drive stator 362 to the first magnet 3642 (under conditions of equal currents) and the torque of the powered stator 366 to the second magnet 3644 (under conditions of equal currents). In addition, the first magnetic core 3622 and the second magnetic core 3664 without the head portions can also greatly reduce the problem of reduction in motor power caused by local magnetic short circuit due to contact between adjacent magnetic cores.

The cross-sectional shapes of the first magnetic core 3622 and the second magnetic core 3664 having only magnetic pillars may be fan-shaped, circular, trapezoidal, triangular, and so on. In the illustrated embodiment, the first magnetic core 3622 and the second magnetic core 3664 having only magnetic pillars are substantially triangular prisms, and one edge of each magnetic core faces the axis of the rotating shaft 35. In the embodiment, edges of the first magnetic core 3622 and the second magnetic core 3664 are rounded. By rounding the edges, the subsequent winding of the coil can be facilitated, and meanwhile, it is beneficial to protect the insulating materials wrapped around the coils.

It should be appreciated that in other embodiments, the first magnetic core 3622 and the second magnetic core 3664 may further include a head portion provided at one end of the magnetic pillar; the first back plate 3625 is engaged with an end of the magnetic pillar of the first magnetic core 3622 away from the head portion. The second back plate 3662 is engaged with an end of the magnetic pillar of the second magnetic core 3664 away from the head portion. Alternatively, in some embodiments, one of the first magnetic core 3622 and the second magnetic core 3664 may have both a magnetic pillar and a head portion, and the other may only have a magnetic pillar.

In the illustrated embodiment, both the first magnet 3642 and the second magnet 3644 are located between the drive stator 362 and the power stator 366. From one end adjacent to the impeller 20 to one end away from the impeller 20, the power stator 366, the second magnet 3644, the first magnet 3642, and the drive stator 362 are arranged in sequence along the axis of the rotating shaft 35.

In the illustrated embodiment, the magnetic assembly 364 further includes a flywheel 3645 fixedly connected to the rotating shaft 35. The flywheel 3645 is located between the power stator 366 and the drive stator 362; the first magnet 3642 and the second magnet 3644 are both provided on the flywheel 3645. That is, the magnetic assembly 364 is located between the power stator 366 and the drive stator 362. By arranging the flywheel 3645, the connection strength between the magnet and the rotating shaft 35 can be increased, and the stability of the rotating shaft 35 can be improved. In addition, by arranging the first magnet 3642 and the second magnet 3644 on the same flywheel 3645, not only the shaking of the rotating shaft 35 during the rotation can be reduced, which makes the rotating shaft 35 more stable during the rotation, but also the structure of the drive device 30 is simplified.

The flywheel 3645 and the rotating shaft 35 can be formed in one piece; alternatively, the flywheel 3645 can also be fixed to the rotating shaft 35 by bonding, welding, or the like.

Figure 11:
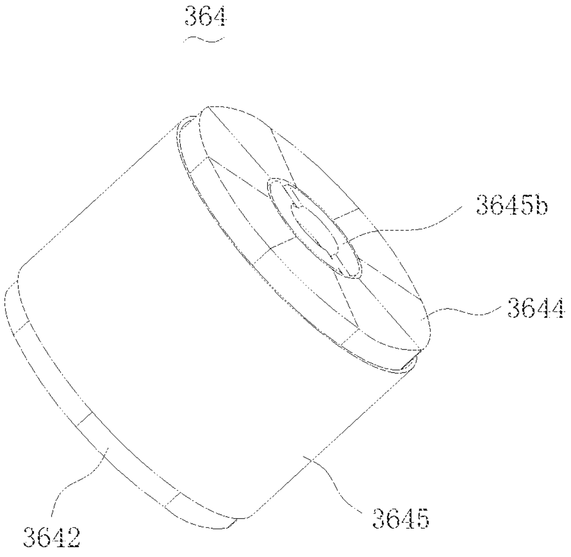
FIG. 11 is a three-dimensional schematic diagram of a magnetic assembly of the blood pump shown in FIG. 3.
Figure 12:
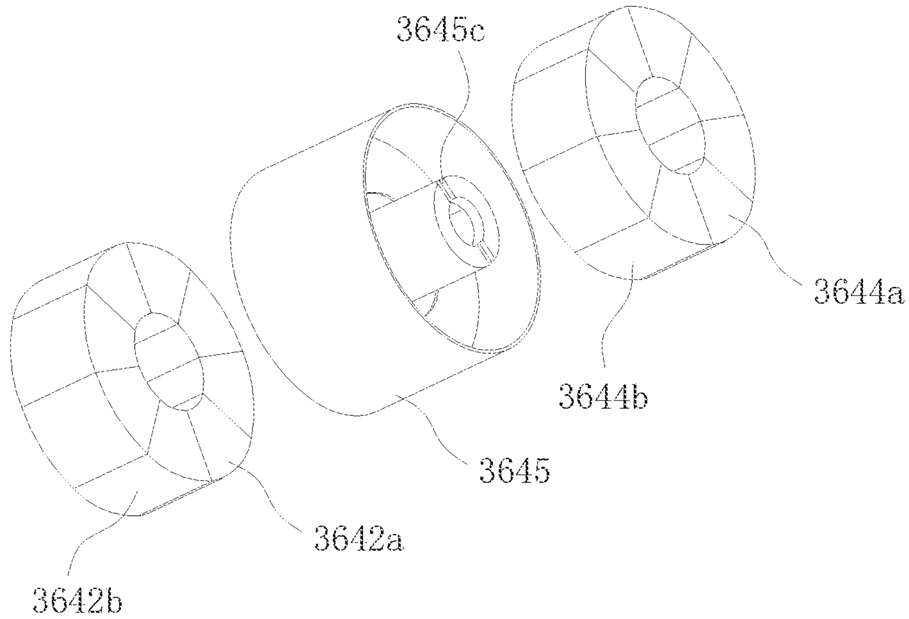
FIG. 12 is an exploded view of the magnetic assembly shown in FIG. 11.
Figure 13:
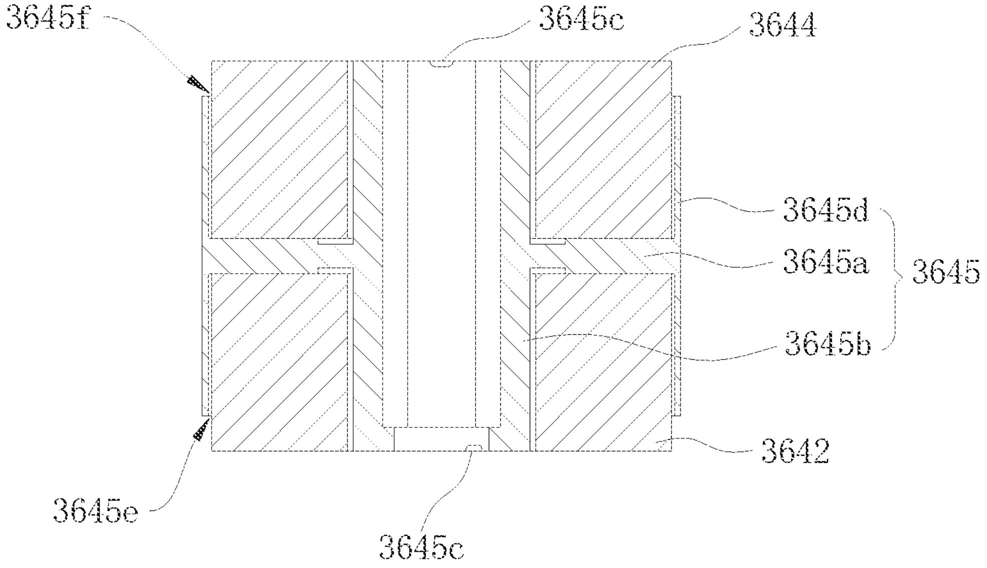
FIG. 13 is a section view of the magnetic assembly shown in FIG. 11.

Referring to FIGS. 11 to 13, in the illustrated embodiments, the flywheel 3645 includes a disc-shaped portion 3645*a* and a tubular portion 3645*b*. The tubular portion 3645*b* fixedly passes through a center of the disc-shaped portion 3645*a*, and is coaxial with the disc-shaped portion 3645*a*. One end of the rotating shaft 35 away from the impeller 20 is fixedly received in the tubular portion 3645*b*; the first magnet 3642 and the second magnet 3644 are respectively arranged on opposite sides of the disc-shaped portion 3645*a*, to facilitate the assembling of the first magnet 3642 and the second magnet 3644 in order to better fix the first magnet 3642 and the second magnet 3644 to the rotating shaft 35.

Specifically, both the first magnet 3642 and the second magnet 3644 are ring-shaped Halbach array magnets. The first magnet 3642 includes a plurality of first magnetic blocks 3642*a* with magnetization directions parallel to the axis of the first magnet 3642; and the second magnet 3644 includes a plurality of second magnetic blocks 3644*a* with magnetization directions parallel to the axis of the second magnet 3644. The plurality of second magnetic blocks 3644*a* and the plurality of first magnetic blocks 3642*a* are respectively arranged on both opposite sides of the disc-shaped portion 3645*a* around the rotating shaft 35. In the extension direction of the rotating shaft 35, each second magnetic block 3644*a* is arranged opposite to a first magnetic block 3642*a*, the second magnetic block 3644*a* and the first magnetic block 3642*a* arranged oppositely have opposite polarities at sides facing the disk-shaped portion 3645*a*. Such arrangement can facilitate the mounting of the first magnet 3642 and the second magnet 3644, and avoid the problem of difficult assembly caused by the mutual repulsion between the magnetic blocks of the first magnet 3642 and the magnetic blocks of the second magnet 3644.

In some embodiments, the first magnet 3642 further includes a plurality of third magnetic blocks 3642*b* magnetized in a circumferential direction of the first magnet 3642. The plurality of third magnetic blocks 3642*b* magnetized in the circumferential direction are arranged alternatively with the plurality of first magnetic blocks 3642*a* magnetized in the direction parallel to the axis of the first magnet 3642 on the circumference. The magnetization directions of adjacent first magnetic blocks 3642*a* are opposite, for example, the magnetization direction of one of the adjacent first magnet blocks 3642*a* is directed from a side of the first magnet block 3642*a* away from the disc-shaped portion 3645*a* toward a side of the first magnet block 3642*a* facing the disk-shaped portion 3645*a*, and the magnetization direction of the other is in a direction from a side of the first magnetic block 3642*a* facing the disk-shaped portion 3645*a* to a side of the first magnetic block 3642*a* away from the disk-shaped portion 3645*a*. The magnetization directions of adjacent third magnetic blocks 3642*b* are opposite on the circumference where the first magnet 3642 is located.

Correspondingly, the second magnet 3644 further includes a plurality of fourth magnetic blocks 3644*b* magnetized in the circumferential direction of the second magnet 3644; the plurality of fourth magnetic blocks 3644*b* are arranged alternatively with the plurality of second magnetic blocks 3644*a* along the circumference where the second magnet 3644 is located. Magnetization directions of adjacent second magnetic blocks 3644*a* are opposite; and magnetization directions of adjacent fourth magnetic blocks 3644*b* are opposite on the circumference where the second magnet 3644 is located.

It should be noted that the magnetization directions of the third magnetic block 3642*b* and the fourth magnetic block 3644*b* are not limited to the circumferential direction of the magnetization, in some embodiments, the magnetization directions of the third magnetic block 3642*b* and the fourth magnetic block 3644*b* may also be inclined with respect to the axis of the rotating shaft 35.

In the illustrated embodiment, the first magnet 3642 and the second magnet 3644 are respectively provided with eight magnetic blocks, that is, there are four first magnetic blocks 3642*a*, four second magnetic blocks 3644*a*, four third magnetic blocks 3642*b*, and four fourth magnetic blocks 3644*b*. The first magnetic block 3642*a*, the second magnetic block 3644*a*, the third magnetic block 3642*b*, and the fourth magnetic block 3644*b* are all fan-ring magnets; the first magnet 3642 and the second magnet 3644 have substantially circular-ring structures. It should be appreciated that, in other embodiments, the first magnet 3642 and the second magnet 3644 may consist of more or less magnetic blocks, such as two, four, six or ten.

In order to facilitate the mounting of the first magnet 3642 and the second magnet 3644, the flywheel 3645 is further provided with an identification portion 3645*c* configured to determine the mounting positions of the first magnetic block 3642*a* and the second magnetic block 3644*a*. The identification portion 3645*c* may be provided as a groove, a scale line or an identifier, etc. When the first magnetic block 3642*a* and the second magnetic block 3644*a* are mounted, only a position of one first magnetic block 3642*a* and a position of one second magnetic block 3644*a* are identified by the identification portion 3645*c*, the mounting positions of the rest of magnetic blocks can be determined, thereby facilitating the mounting of the first magnet 3642 and the second magnet 3644. Specifically, the identification portion 3645*c* may be on at least one of the tubular portion 3645*b* and the disc-shaped portion 3645*a*. Specifically, in the illustrated embodiment, both ends of the tubular portion 3645*b* are provided on the identification portion 3645*c*.

In the embodiment, the flywheel 3645 may further include an outer ring wall 3645*d* arranged around the disc-shaped portion 3645*a*. The outer ring wall 3645*d*, the tubular portion 3645*b*, and the disc-shaped portion 3645*a* together enclose a first receiving portion 3645*e* configured to receive the first magnet 3642 and a second receiving portion 3645*f* configured to receive the second magnet 3644. The first receiving portion 3645*e* and the second receiving portion 3645*f* are separated by the disc-shaped portion 3645*a*. Such arrangement can limit the positions of the first magnet 3642 and the second magnet 3644, which not only facilitates the mounting of the first magnet 3642 and the second magnet 3644, but also makes the combinations of the first magnet 3642, the second magnet 3644 and the flywheel 3645 more stable.

In the embodiment, in the axial direction of the tubular portion 3645*b*, a side of the first magnet 3642 away from the disc-shaped portion 3645*a* is higher than the outer ring wall 3645*d* by a certain distance, and a side of the second magnet 3644 away from the disc-shaped portion 3645*a* is higher than the outer ring wall 3645*d* by a certain distance, in order to facilitate the assembly of the first magnet 3642 and the second magnet 3644 onto the flywheel 3645.

It should be noted that the flywheel 3645 is not limited to the above structure. In some embodiments, the flywheel 3645 does not have the outer ring wall 3645*d*. In some embodiments, the flywheel 3645 does not have the outer ring wall 3645*d* and the tubular portion 3645*b*, under this condition, the rotating shaft 35 is fixedly passed through the disc-shaped portion 3645*a*, for example, the center of the disc-shaped portion 3645*a*. Compared to the flywheel 3645 having only the disk-shaped portion 3645*a*, the provided tubular portion 3645*b* can allow a more stable connection between the flywheel 3645 and the rotating shaft 35.

Figure 14:
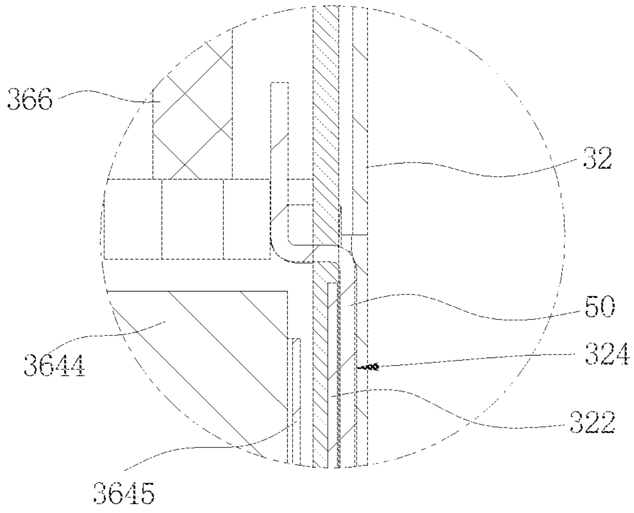
FIG. 14 is an enlarged view of a portion I shown in FIG. 3.
Figure 15:
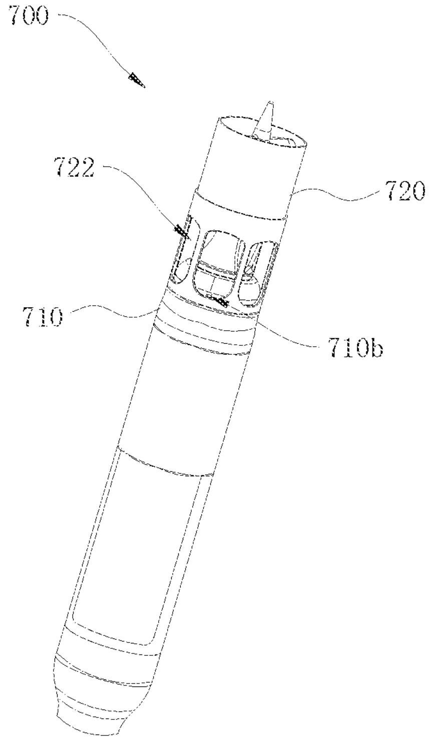
FIG. 15 is a partial schematic diagram of a blood pump according to an embodiment II.
Figure 16:
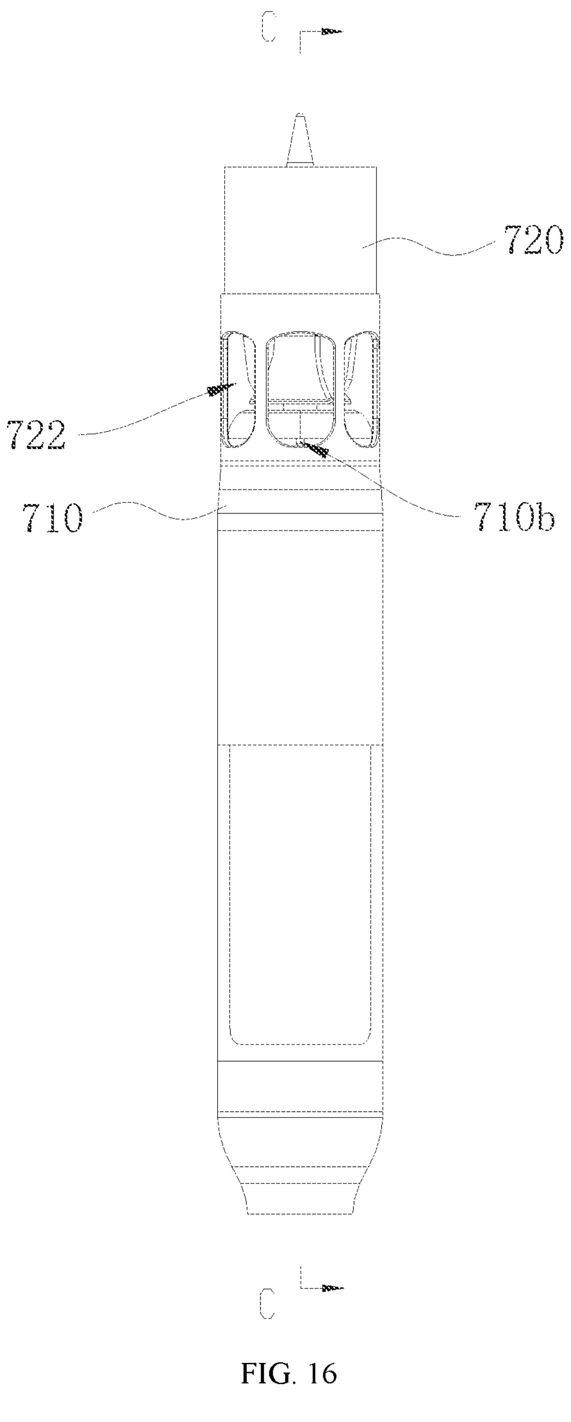
FIG. 16 is a schematic structure diagram of the blood pump shown in FIG. 15 from another perspective.
Figure 17:
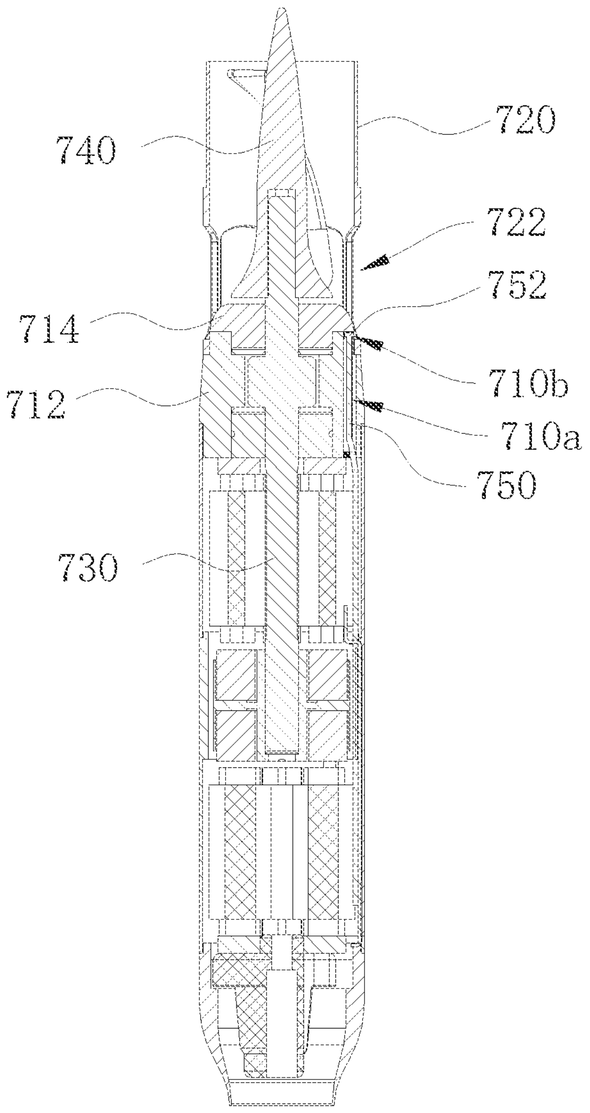
FIG. 17 is a section view of FIG. 16 along C-C.
Figure 18:
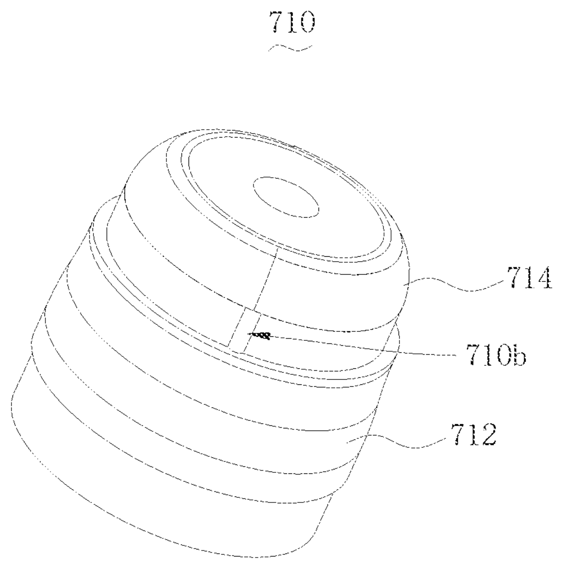
FIG. 18 is a schematic structure view of the shaft sleeve assembly of the blood pump shown in FIG. 15.
Figure 19:
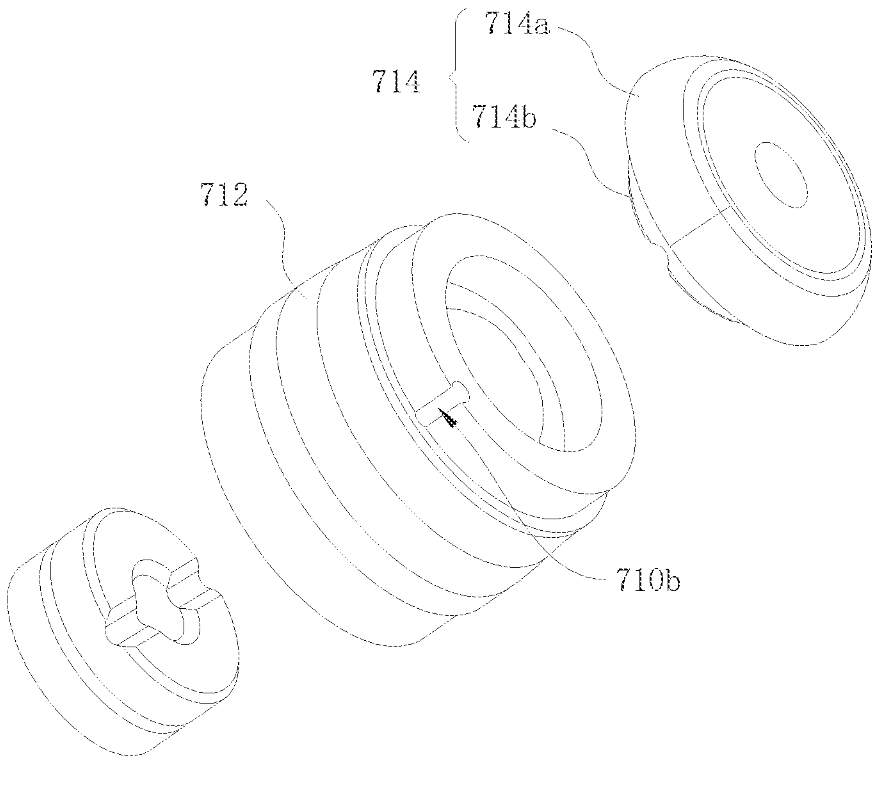
FIG. 19 is an exploded view of the shaft sleeve assembly shown in FIG. 18.
Figure 20:
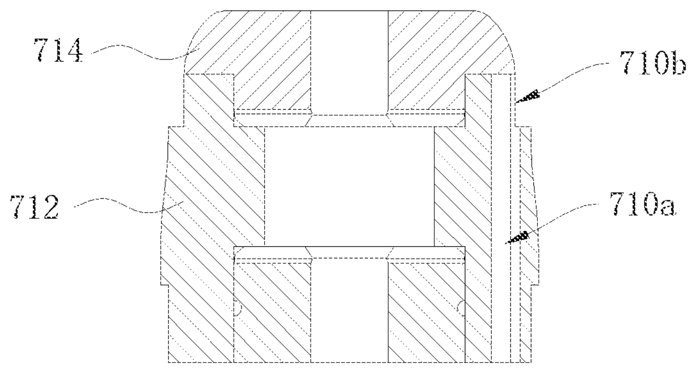
FIG. 20 is a section view of the shaft sleeve assembly shown in FIG. 18.

Referring to FIG. 14, it is usually necessary to provide an electric wire 50 to electrically connect the power stator 366 to supply power to the power stator 366 and/or to control the power stator 366. The electric wire 50 connected to the power stator 366 is usually extended inside the drive housing 32 and toward an end of the drive housing 32 away from the impeller 20. The magnetic assembly 364 is provided between the power stator 366 and the drive stator 362. If the electric wire 50 connected to the power stator 366 is in contact with the rotated magnetic assembly 364, there may be a risk that as the magnetic assembly 364 rotates, the electric wire 50 electrically connected to the power stator 366 may be twisted or dropped.

For this purpose, a protection portion 322 is fixed inside the drive housing 32, and a position of the protection portion 322 corresponds to the position of the magnetic assembly 364. A protection gap 324 is formed between the protection portion 322 and the inner wall of the drive housing 32. The electric wire 50 passes through the protection gap 324 and is electrically connected to the power stator 366. The protection portion 322 is located between the magnetic assembly 364 and the electric wire 50. By arranging the protection portion 322, the risk that the electric wire 50 may be twisted or dropped as the magnetic assembly 364 rotates due to the electric wire 50 being in contact with the magnetic assembly 364 during the rotation of the magnetic assembly 364 can be avoided. In some embodiments, one end of the electric wire 50 is electrically connected to the second coil 3665 of the power stator 366, and the other end is electrically connected to an external controller of the blood pump 100.

It should be noted that, in order to prevent the electric wire 50 from rotating with the magnetic assembly 364, it is not limited to adopt the mode of arranging the protection portion 322. In some embodiments, a channel can also be directly provided on a side wall of the drive housing 32 for the electric wire 50 to pass through. In this case, there is no need to provide the protection portion 322.

It should be noted that the drive component 36 is not limited to the above-mentioned structure. In some embodiments, the magnetic assembly 364 has two flywheels, and the power stator 366 is located between the two flywheels, that is, one flywheel is located between the impeller 20 and the power stator 366, and the other flywheel is located between the power stator 366 and the drive stator 362. The first magnet 3642 is fixed on the flywheel between the power stator 366 and the drive stator 362, and the second magnet 3644 is fixed on the flywheel between the impeller 20 and the power stator 366. In this case, if the protection portion 322 is provided, the protection portion 322 is provided between the drive housing 32 and the flywheel located between the power stator 366 and the drive stator 362, that is, the position of the protection portion 322 corresponds to the position of the first magnet 3642. In this case, the protection portion 322 is located between the flywheel configured to mount the first magnet 3642 and the electric wire 50. It should be appreciated that in this case, the magnetic assembly 364 may not have a flywheel, under this condition, the protection portion 322 is located between the first magnet 3642 and the electric wire 50.

Alternatively, in some embodiments, the two flywheels are both located between the drive stator 362 and the power stator 366, and the two flywheels are respectively configured to mount the first magnet 3642 and the second magnet 3644. In this case, if a protection portion 322 is provided, a protection portion 322 is provided between the flywheel configured to mount the first magnet 3642 and the electric wire 50, and a protection portion 322 is provided between the flywheel configured to mount the second magnet 3644 and the electric wire 50. It should be appreciated that the magnetic assembly 364 may not have a flywheel, and in this case, the protection portions 322 are provided respectively between the first magnet 3642 and the electric wire 50, and between the second magnet 3644 and the electric wire 50.

Alternatively, in some embodiments, the magnet assembly 364 includes one flywheel, one of the first magnet 3642 and the second magnet 3644 is mounted on the flywheel, and the other is directly mounted on the rotating shaft 35.

Alternatively, in some embodiments, the drive component 36 only includes one of the drive stator 362 and the power stator 366, for example, the drive component 36 only includes the drive stator 362, without the power stator 366, and in this case, the magnetic assembly 364 does not include the second magnet 3644; the magnetic assembly 364 is located between the impeller 20 and the drive stator 362, in this case, there is no need to provide the protection portion 322. For another example, the drive component 36 only includes the power stator 366, in this case, the magnetic assembly 364 does not include the first magnet 3642, in this case, the magnetic assembly 364 can be arranged between the impeller 20 and the power stator 366, or the power stator 366 can also be arranged between the impeller 20 and the magnetic assembly 364. If the magnetic assembly 364 is arranged between the impeller 20 and the power stator 366, the electric wire 50 electrically connected to the power stator 366 does not pass through the magnetic assembly 364, then there is no need to provide the protection portion 322. If the power stator 366 is arranged between the impeller 20 and the magnetic assembly 364, in order to prevent the electric wire 50 from rotating with the magnetic assembly 364, the protection portion 322 is preferably provided.

Alternatively, in some embodiments, the rotating shaft 35 may also be configured to pass through the drive stator 362, in this case, the drive component 36 may also include the power stator 366 or may not include the power stator 366. When the drive component 36 does not include the power stator 366, in this case, the arrangement mode of the drive stator 362 may be consistent with that of the drive component 36 including only the power stator 366. When the drive component 36 simultaneously includes the drive stator 362 and the power stator 366, and the rotating shaft 35 passes through the drive stator 362 and the power stator 366, in this case, the magnetic assembly 364 can be arranged between the drive stator 362 and the power stator 366; alternatively, the power stator 366 is located between the first magnet 3642 and the second magnet 3644; alternatively, the power stator 366 and the drive stator 362 are located between the first magnet 3642 and the second magnet 3644.

Referring to FIG. 3 and FIG. 4, the sensor assembly 40 can detect a fluid pressure outside the drive device 30, and the external fluid pressure can be configured to determine whether the drive device 30 is located at a target position, that is, to determine whether the blood pump 100 is located at the target position. For example, the fluid pressure is configured to detect whether the blood pump 100 reaches the target position during the delivery of the blood pump 100, or to detect the position of the blood pump 100 in real time when the blood pump 100 is working, in order to adjust the position of the blood pump 100 in time when the blood pump 100 deviates from the target position. The sensor assembly 40 includes a sensor 42; the sensor 42 includes a probe 422; the probe 422 is received in the receiving cavity 34*a*; the position of the probe 422 corresponds to the position of a detection port 34*b*; and the probe 422 can detect the fluid pressure outside the drive device 30. Specifically, the probe 422 is sealed within the receiving cavity 34*a*.

Specifically, the sensor 42 is a fiber optic pressure sensor. The optical fiber pressure sensor has the advantages of no electromagnetic interference, small size, reliable measurement, high precision and corrosion resistance, and is especially suitable for a blood pump with an outer diameter of no more than 10 mm such as the intravascular blood pump.

Specifically, the sensor 42 may further include a transmission fiber 424 connected to the probe 422. One end of the transmission fiber 424 adjacent to the probe 422 is received in the receiving cavity 34*a*. In the illustrated embodiment, the receiving cavity 34*a* is provided with a communication port 34*c*, and the transmission fiber 424 passes through the communication port 34*c*. One end of the transmission fiber 424 is received in the receiving cavity 34*a* and connected to the probe 422, and the other end extends into the drive housing 32 from the communication port 34*c*. Specifically, a portion of the transmission fiber 424 outside the receiving cavity 34*a* passes through the drive housing 32, and extends out of the drive housing 32 from an end of the drive housing 32 away from the shaft sleeve assembly 24.

In some embodiments, the sensor assembly 40 further includes a packaging tube 43. The portion of the transmission fiber 424 outside the receiving cavity 34*a* is packaged in the packaging tube 43. Generally, the material of the transmission fiber 424 of the fiber optic pressure sensor is usually a glass fiber, which is brittle and easily broken. The portion of the transmission fiber 424 outside the receiving cavity 34*a* is packaged by using the packaging tube 43, which can effectively protect the transmission fiber 424. Since the portion of the transmission fiber 424 in the receiving cavity 34*a* is protected by the cavity wall of the receiving cavity 34*a*, there is no need to provide the packaging tube 43 on the portion of the transmission fiber 424 located in the receiving cavity 34*a*, accordingly, the size of the receiving cavity 34*a* is reduced. In an embodiment, the packaging tube 43 is a PI packaging tube.

Specifically, the sensor assembly 40 may further include a soft filler 44. The soft filler 44 is provided between the probe 422 and the cavity wall of the receiving cavity 34*a* to prevent a rigid contact between the probe 422 and the cavity wall of the receiving cavity 34*a* in order to protect the probe 422.

Specifically, a soft filler 44 is further provided at the detection port 34*b*, and the soft filler 44 at the detection port 34*b* seals the detection port 34*b* and can transmit the received fluid pressure to the probe 422. That is, the soft filler 44 at the detection port 34*b* functions to seal the detection port 34*b* to prevent the fluid outside the blood pump 100 from entering the receiving cavity 34*a* through the detection port 34*b*, and also functions to transmit the pressure to the probe 422. In order to enable the external fluid pressure to be better transmitted to the probe 422 through the soft filler 44 at the detection port 34*b*, the soft filler 44 is in close contact with the probe 422.

In some embodiments, the material of the soft filler 44 may be, for example, silicone, etc.

In the illustrated embodiment, the blood pump 100 may further include a catheter assembly 60 fixed to the drive housing 32. The catheter assembly 60 can pass perfusate into the drive housing 32, and there is a gap between the rotating shaft 35 and the shaft sleeve assembly 34 for the perfusate to pass through. The perfusate that the catheter assembly 60 passes into the drive housing 32 can flow out of the drive housing 32 through the gap between the rotating shaft 35 and the shaft sleeve assembly 34, and enter the cannula assembly 10. Specifically, the perfusate passed into the drive housing 32 by the catheter assembly 60 passes through the drive housing 32, and flows through the gap between the second shaft sleeve 346 and the rotating shaft 35, the gap between the convex ring 354 of the rotating shaft 35 and the protrusion 3422 of the adapter sleeve 342 in sequence, and the gap between the rotating shaft 35 and the first shaft sleeve 344, and flows into the cannula assembly 10 through the gap between the rotating shaft 35 and the first shaft sleeve 344.

The perfusate not only functions to prevent the blood in the cannula assembly 10 from entering the drive housing 35 through the gap between the rotating shaft 35 and the first shaft sleeve 344, but also serves as lubrication between the second shaft sleeve 346 and the rotating shaft 35, and between the rotating shaft 35 and the first shaft sleeve 344.

Specifically, a supply pipe communicating with the drive housing 32 is provided in the catheter assembly 60, and the supply pipe is configured to pass the perfusate into the drive housing 32.

In some embodiments, the perfusate can be, for example, physiological saline, physiological saline containing heparin, or glucose, etc.

Specifically, the gap between a hole wall of the first shaft hole 344*a* and the rotating shaft 35 is less than or equal to 2 μm. Since the smallest red blood cells (about 8 μm in diameter and about 2 μm in thickness) are difficult to enter the gap with a width less than or equal to 2 μm, and a cleaning fluid for backwashing passes through this gap, which can more effectively prevent the blood from entering the interior of the drive housing 32 through the first shaft hole 344*a*.

In order to prevent the perfusate from contaminating and/or corroding the components in the drive device 30, the drive components 36 (e.g., the drive stator 362 and the power stator 366, etc.) of the drive device 30 are covered with a waterproof sealing film. A material of the waterproof sealing film may be a film formed by silica gel or glue.

Specifically, the catheter assembly 60 may further include an electrical connection wire electrically connected to the drive device 30 (for example, an electrical connection wire electrically connecting the drive device 30 to an external controller). Specifically, both the supply pipe and the electrical connection wire extend into the drive housing 32 from an end of the drive housing 32 away from the open end. The electric wire 50 may be directly electrically connected to the electrical connection wire or indirectly electrically connected to the electrical connection wire.

In order to prevent the perfusate from entering the receiving cavity 34*a* from the drive housing 35 to affect the detection accuracy of the probe 422 of the receiving cavity 34*a*, a sealing element 326 is provided at the communication port 34*c*, and the sealing element 326 prevents the receiving cavity 34*a* from communicating with the drive housing 32 through the communication port 34*c*, to prevent the perfusate in the drive housing 32 from entering the receiving cavity 34*a* through the communication port 34*c* to affect the detection accuracy of the probe 422 for the external fluid pressure. Specifically, the portion of the transmission fiber 424 outside the receiving cavity 34*a* and the drive housing 35 is received in the catheter assembly 60, and is extended to the outside of the patient with the catheter assembly 60 and is connected to an external controller.

Figure 6:
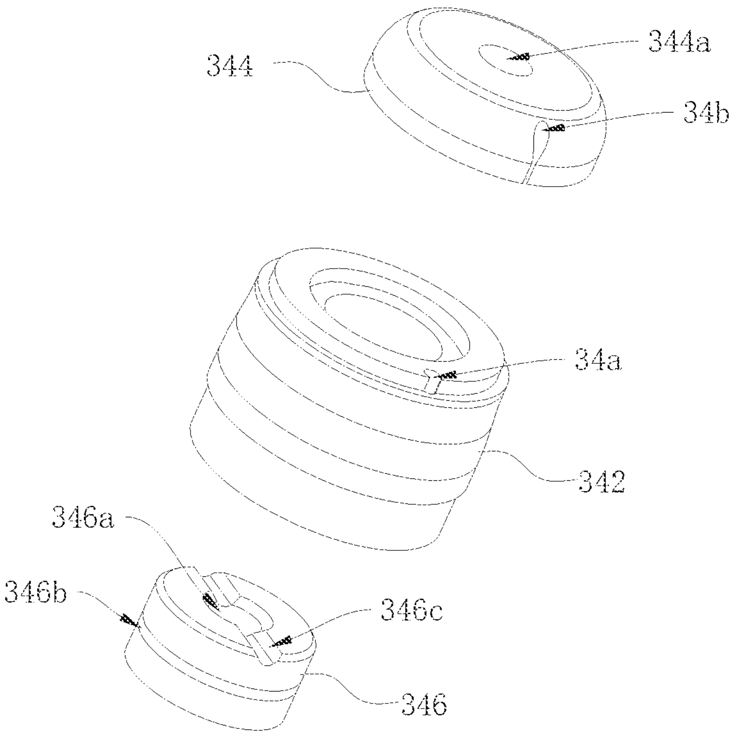
FIG. 6 is an exploded view of the shaft sleeve assembly shown in FIG. 5.
Figure 7:
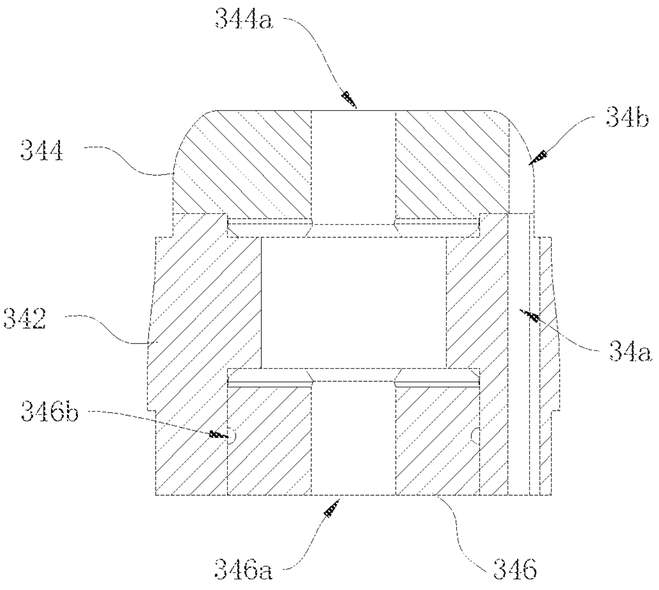
FIG. 7 is a section view of the shaft sleeve assembly shown in FIG. 5.
Figure 8:
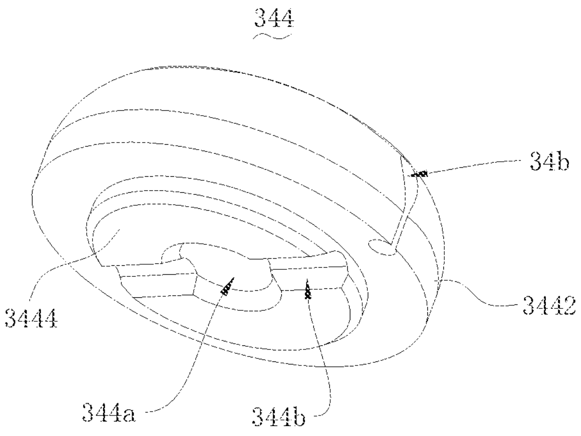
FIG. 8 is a schematic structure diagram of a first shaft sleeve of the shaft sleeve assembly shown in FIG. 5.

Referring to FIG. 6 and FIG. 8, further, a first fluid groove 344*b* is provided on a side of the first shaft sleeve 344 adjacent to the convex ring 354, and the first fluid groove 344*b* is communicated with the gap between the first shaft sleeve 344 and the rotating shaft 35. Specifically, the first fluid groove 344*b* is located at an end of the convex plate 3444 away from the cap portion 3442. A second fluid groove 346*c* is provided on a side of the second shaft sleeve 346 adjacent to the convex ring 354, and the second fluid groove 346*c* is communicated with the gap between the second shaft sleeve 346 and the rotating shaft 35. In such a manner, the circulation of the perfusate is facilitated. It should be noted that, in other embodiments, one of the first shaft sleeve 344 and the second shaft sleeve 346 may be provided with the fluid groove, or neither is provided with the fluid groove.

The above-mentioned blood pump 100 has at least the following advantages:

(1) The shaft sleeve assembly 34 of the above-mentioned drive device 30 is provided with a receiving cavity 34*a* and a detection port 34*b* communicated with the receiving cavity 34*a*, and the probe 422 of the sensor 42 of the sensor assembly 40 is received in the receiving cavity 34*a*, and the position of the probe 422 corresponds to the position of the detection port 34*b*, and the detection port 34*b* is located on the outer wall of the shaft sleeve assembly 34, to enable the probe 422 to detect the fluid pressure outside the drive device 30 at the detection port 34*b*, so that the operator can determine whether the drive device 30 is located at the target position more accurately according to the value of the detected external fluid pressure, in order to facilitate the delivery of the blood pump 100 and the adjustment of the position of the blood pump 100. The sensor probe 422 is received in the receiving cavity 34*a* provided on the shaft sleeve assembly 34, to integrate the probe 422 in the shaft sleeve assembly 34, thereby avoiding the problem of increased diameter of the drive device 30 caused by adding the sensor assembly 40 onto the drive device 30. Therefore, the above-mentioned blood pump 100 can not only detect the position of the blood pump 100 more accurately, but also has a smaller diameter.

(2) By sealing the probe 422 of the sensor 42 of the sensor assembly 40 in the receiving cavity 34*a* of the shaft sleeve assembly 34, not only the perfusate in the drive housing 32 can be effectively prevented from entering the receiving cavity 34*a* to affect the detection accuracy of the probe 422 for the external fluid pressure, but also the external fluid (such as blood) of the blood pump 100 can be prevented from entering the receiving cavity 34*a* through the detection port 34*b* to contaminate the sensor 42, or from entering the drive housing 32 through the receiving cavity 34*a* to contaminate the components inside the drive housing 32.

(3) Since the position of the probe 422 corresponds to the position of the detection port 34*b*, and the position of the detection port 34*b* is adjacent to the outflow port 14 or the position of the detection port 34*b* corresponds to the position of the outflow port 14, the more adjacent the probe 422 is to the outflow port 14 of the cannula assembly 10, the more directly the data detected by the probe 422 can be configured to determine the position of the blood pump 100, and the detected data is more accurate.

(4) The portion of the transmission fiber 424 of the above-mentioned blood pump 100 outside the receiving cavity 34*a* passes through the drive housing 32, and is extended out of the drive housing 32 from the end of the drive housing 32 away from the cannula assembly 10, so that the portion of the sensor assembly 40 mounted in the blood pump 100 is integrated inside the drive device 30, thereby protecting the transmission assembly 40.

(5) By spacing the drive stator 362 and the rotating shaft 35 along the axis of the rotating shaft 35, that is, the rotating shaft 35 is not inserted into the drive stator 362, so that the cross-section of the magnetic core of the drive stator 362 is set larger, which is beneficial to reduce the power consumption of the whole blood pump 100 and the heat generation.

As shown in FIGS. 15 to 20, the blood pump 700 in the second embodiment is substantially the same in structure as the blood pump 100 in the first embodiment, but the difference lies in that the receiving cavity 710*a* and the detection port 710*b* of the shaft sleeve assembly 710 of the blood pump 700 in the second embodiment are both located on the adapter sleeve 712, and the detection port 710*b* is located on the outer peripheral wall of the end of the adapter sleeve 712 adjacent to the cap portion 714*a* of the first shaft sleeve 714. The position of the detection port 710*b* also corresponds to the position of the outflow port 722 of the cannula assembly 720. Moreover, the surface of the cap portion 714*a* of the first shaft sleeve 714 on which the convex plate 714*b* is formed abuts against the end surface of the adapter sleeve 712 away from the drive housing.

Assuming that the extension direction of the axis of the rotating shaft 730 is the axial direction of the blood pump 700, and the direction perpendicular to the axis of the rotating shaft 730 is the radial direction, then the detection port 710*b* in this embodiment is arranged radially, which can reduce the effect of the pressure on the probe 752 of the sensor assembly 750 caused by the blood flow due to the rotation of the impeller 740. In other words, the arrangement mode of the detection port 710*b* in the embodiment can detect the external fluid pressure more accurately not only when the blood pump 700 is delivered, but also when the blood pump 700 operates.

Since the structure of the blood pump 700 in the second embodiment is similar to the structure of the blood pump 100 in the first embodiment, the blood pump 700 in the second embodiment also has the advantages of the blood pump in the first embodiment, which will not be repeated here.

Figure 21:
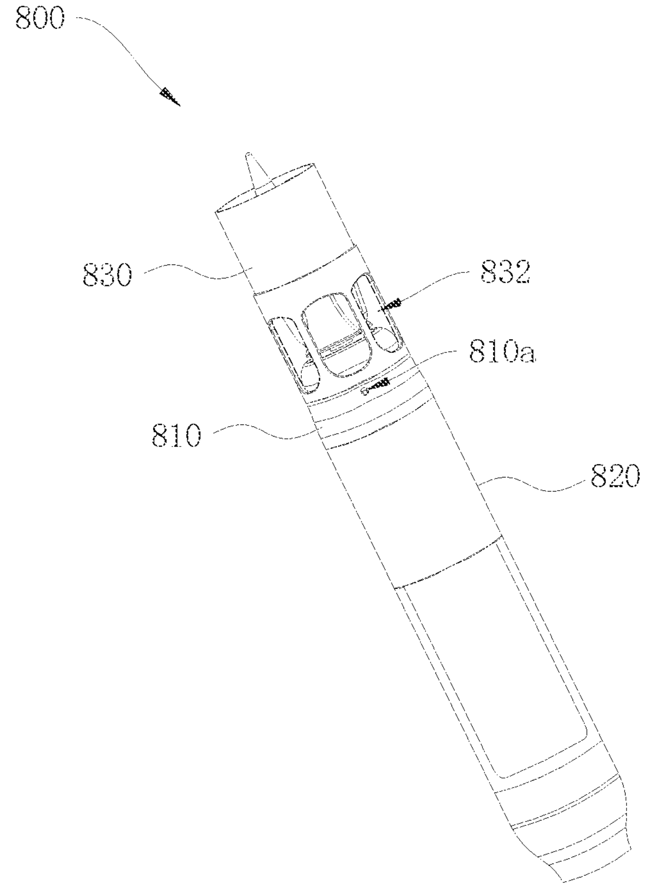
FIG. 21 is a partial schematic diagram of a blood pump according to an embodiment III.
Figure 22:
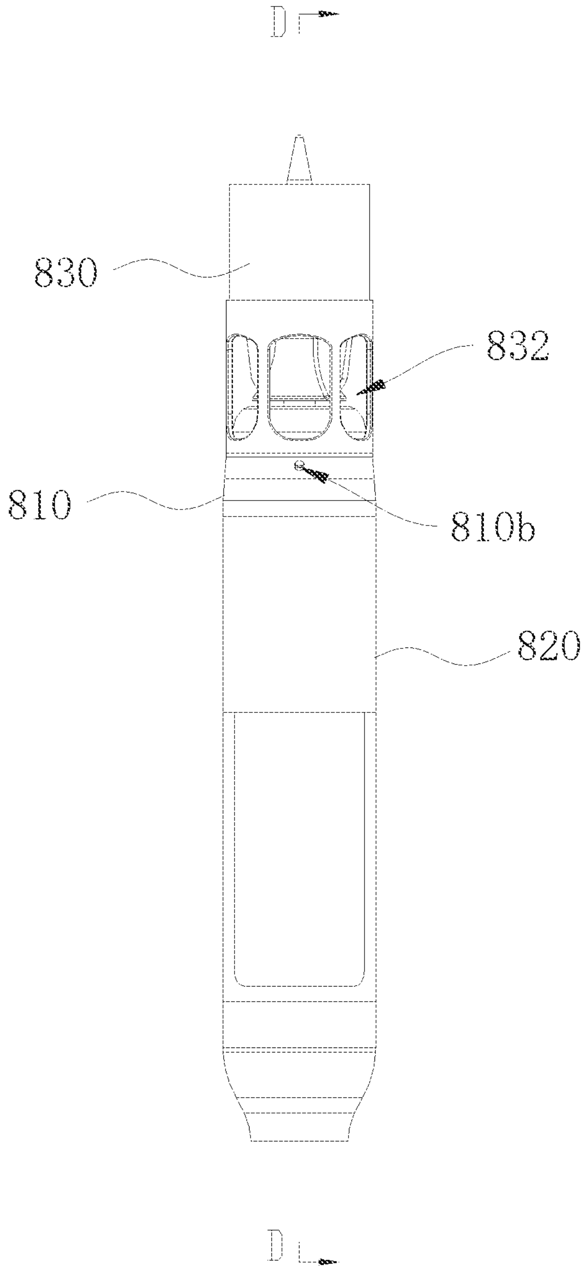
FIG. 22 is a schematic structure diagram of the blood pump shown in FIG. 21 from another perspective.
Figure 23:
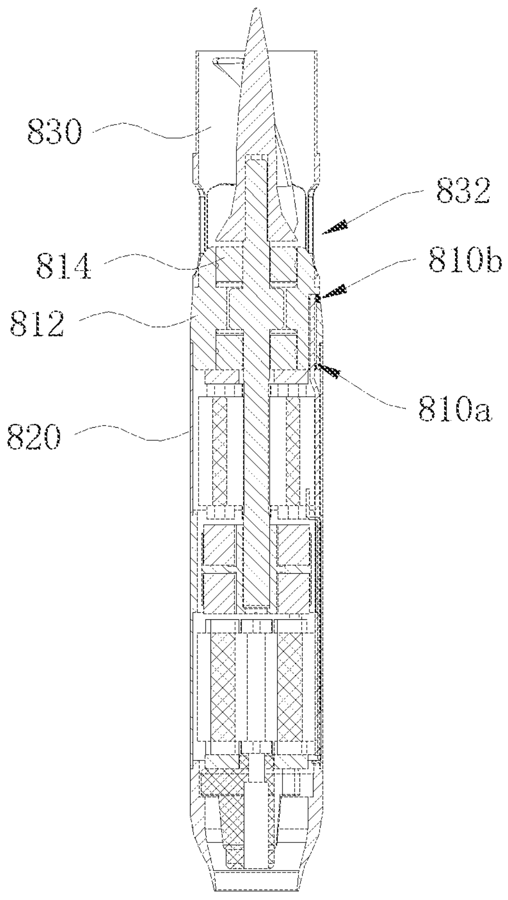
FIG. 23 is a section view of FIG. 22 along D-D.

As shown in FIGS. 21 to 23, the blood pump 800 in the third embodiment has substantially the same structure as the blood pump 100 in the first embodiment, but the difference lies in that the structure of the shaft sleeve assembly 810 of the blood pump 800 in the third embodiment is slightly different from the structure of the shaft sleeve assembly 34 of the blood pump 100 in the first embodiment. More specifically, the structures of the adapter sleeve 812 and the first shaft sleeve 814 of the shaft sleeve assembly 810 in this embodiment are different from the structures of the adapter sleeve 342 and the first shaft sleeve 344 of the shaft sleeve assembly 34 of the blood pump 100 in the first embodiment.

Figure 24:
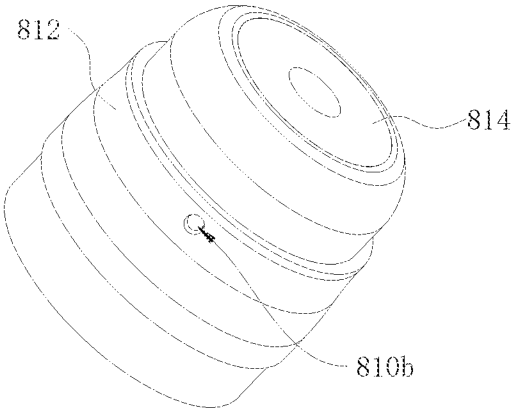
FIG. 24 is a schematic structure diagram of a shaft sleeve assembly of the blood pump shown in FIG. 21.
Figure 25:
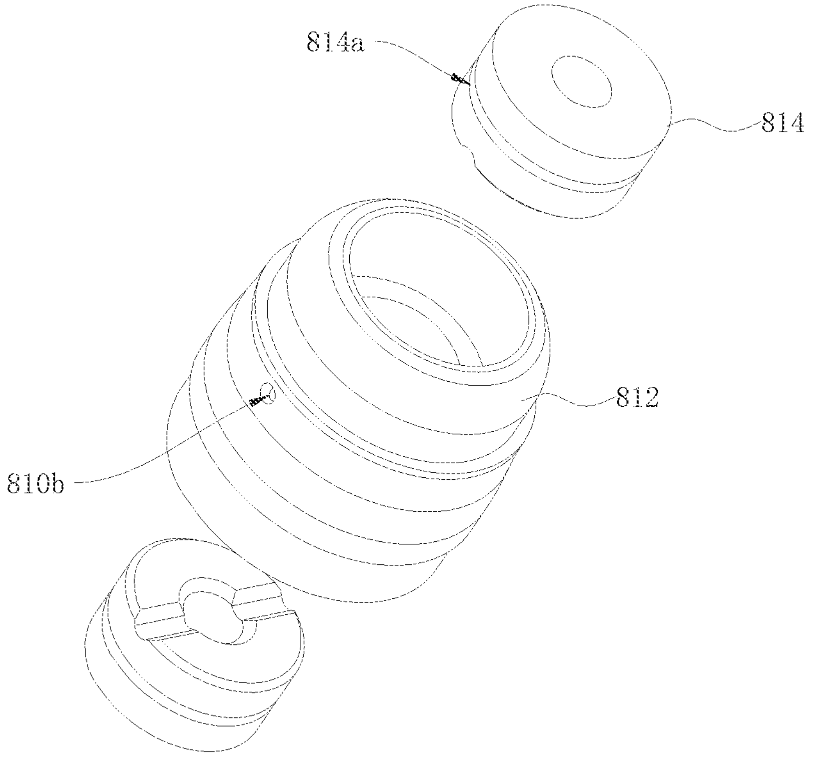
FIG. 25 is an exploded view of the shaft sleeve assembly shown in FIG. 24.
Figure 26:
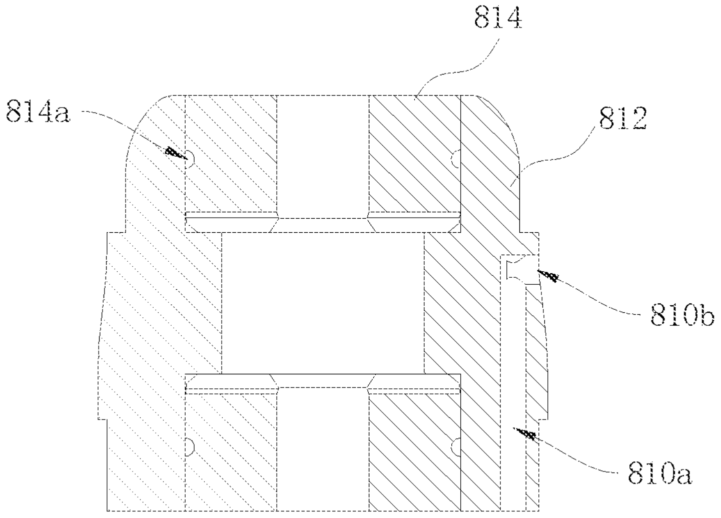
FIG. 26 is a section view of the shaft sleeve assembly shown in FIG. 24.

Referring to FIG. 24 to FIG. 26, in the embodiment, the first shaft sleeve 814 does not include a cap portion, and the first shaft sleeve 814 substantially has a disc-shaped structure. The first shaft sleeve 814 is fixedly received in the adapter sleeve 812. The first shaft sleeve 814 is provided on the end of the adapter sleeve 812 away from the drive housing 820, and the outer wall of the first shaft sleeve 814 is fixedly connected to the inner wall of the adapter sleeve 812.

Specifically, the first shaft sleeve 814 is bonded and fixed to the adapter sleeve 812 by an adhesive. In the illustrated embodiment, in order to fix the first shaft sleeve 814 in the adapter sleeve 812, the outer peripheral wall of the first shaft sleeve 814 is provided with a glue groove 814*a* configured to receive the adhesive.

Both the receiving cavity 810*a* and the detection port 810*b* are located on the adapter sleeve 812. In the illustrated embodiment, the detection port 810*b* is located on the outer peripheral wall of the adapter sleeve 812. The detection port 810*b* in this embodiment is arranged radially. Accordingly, the probe in this embodiment can detect the position of the blood pump 800 more accurately even when the blood pump 800 is working.

It should be appreciated that, in other embodiments, the detection port 810*b* may also be located on the end face of the end of the adapter sleeve 812 away from the drive housing 820, so that the detection port 810*b* is more adjacent to the outflow port 832 of the cannula assembly 830, so that it is convenient to detect the position of the blood pump 800 more accurately and directly when the blood pump 800 is delivered.

Since the structure of the blood pump 800 in the third embodiment is similar to the structure of the blood pump 100 in the first embodiment, the blood pump 800 in the third embodiment also has the advantages of the blood pump 100 in the first embodiment, and which will not be repeated here.

The above embodiments are merely used for illustrating the technical solution of the present disclosure, rather than to limit it. Although the present disclosure has been described in detail with reference to the foregoing embodiments, those of ordinary skill in the art should understand that the technical solution described in the foregoing embodiments can still be modified, or equivalent replacement is performed on some of the technical features; and these modifications or replacements do not make the essence of the corresponding technical solution deviate from the spirit and scope of the technical solution of each embodiment of the present disclosure, and accordingly should be regarded as the protection scope of the present disclosure.

What is claimed is:

1. A drive device, comprising:

a drive housing;

a shaft sleeve assembly fixedly connected to the drive housing, wherein the shaft sleeve assembly is provided with a receiving cavity and a detection port communicated with the receiving cavity, and the detection port is located on an outer wall of the shaft sleeve assembly;

a rotating shaft, rotatably passing through the shaft sleeve assembly;

a drive component, mounted on the drive housing and capable of driving the rotating shaft to rotate; and a sensor assembly comprising a sensor, the sensor comprising a probe, wherein the probe is received in the receiving cavity, a position of the probe corresponds to a position of the detection port, and the probe is capable of detecting a fluid pressure outside the drive device, wherein the shaft sleeve assembly comprises an adapter sleeve and a first shaft sleeve, the adapter sleeve is fixedly connected to the drive housing, the first shaft sleeve is fixedly connected to the adapter sleeve, and the rotating shaft is capable of rotatably passing through the first shaft sleeve and the adapter sleeve, and wherein the receiving cavity is at least partially located on the first shaft sleeve, and the detection port is at least partially located on the first shaft sleeve; or both the receiving cavity and the detection port are located on the adapter sleeve.

2. The drive device according to claim 1, wherein the first shaft sleeve comprises a disc-shaped cap portion and a convex plate, the cap portion is provided with a first surface and a second surface facing away from each other, the convex plate is formed on the first surface, the first shaft sleeve is provided with a first shaft hole, the first shaft hole extends from an end surface of an end of the convex plate away from the cap portion to the second surface of the cap portion, the cap portion sealingly covers an opening at an end of the adapter sleeve, the drive housing is sheathed to an end of the adapter sleeve away from the cap portion, and the rotating shaft is capable of rotatably passing through the first shaft hole and the adapter sleeve, and wherein, the receiving cavity is extended from the end surface of the end of the adapter sleeve away from the cap portion to the cap portion, the detection port is at least partly located on the cap portion; or, the receiving cavity and the detection port are both located on the adapter sleeve, and the detection port is located at an end of the adapter sleeve adjacent to the cap portion.

3. The drive device according to claim 1, wherein the first shaft sleeve is fixedly received in the adapter sleeve, the receiving cavity and the detection port are both located on the adapter sleeve, and the detection port is arranged at an end of the adapter sleeve away from the drive housing.

4. The drive device according to claim 1, wherein the shaft sleeve assembly further comprises a second shaft sleeve, the second shaft sleeve is fixedly connected to the adapter sleeve, the second shaft sleeve and the first shaft sleeve are arranged along an axis of the rotating shaft, and the rotating shaft is capable of rotatably passing through the second shaft sleeve.

5. The drive device according to claim 4, wherein the first shaft sleeve is provided with a first shaft hole, the second shaft sleeve is provided with a second shaft hole, the rotating shaft comprises a shaft body and a protruding ring arranged around the shaft body for one circle, the shaft body is capable of rotatably passing through the first shaft hole, the second shaft hole, and the adapter sleeve, an end of the shaft body is extended into the drive housing, the protruding ring is located between the first shaft sleeve and the second shaft sleeve, an outer diameter of the protruding ring is greater than a hole diameter of the first shaft hole and greater than a hole diameter of the second shaft hole.

6. The drive device according to claim 1, wherein the sensor assembly further comprises a soft filler, wherein, the soft filler is provided between the probe and a cavity wall of the receiving cavity; and/or, the soft filler is provided at the detection port, the soft filler seals the detection port, and the soft filler is capable of transmitting the received fluid pressure to the probe.

7. The drive device according to claim 1, wherein the sensor is an optical fiber pressure sensor, the sensor further comprises a transmission fiber connected to the probe, and an end of the transmission fiber adjacent to the probe is received in the receiving cavity.

8. The drive device according to claim 7, wherein the receiving cavity further comprises a communication port, the transmission fiber passes through the communication port, one end of the transmission fiber is received in the receiving cavity and is connected to the probe, the other end of the transmission fiber is extended from the communication port into the drive housing, a sealing element is provided at the communication port, and the sealing element prevents the receiving cavity from being communicated with the drive housing through the communication port.

9. The drive device according to claim 7, wherein the sensor assembly further comprises a packaging tube, a portion of the transmission fiber outside the receiving cavity is packaged in the packaging tube.

10. The drive device according to claim 1, wherein the drive component comprises a drive stator and a magnetic assembly, the drive stator is fixedly connected to the drive housing, the drive stator and the rotating shaft are spaced along an axis of the rotating shaft, the magnetic assembly comprises a first magnet, the first magnet is fixedly connected to the rotating shaft, wherein the drive stator is capable of generating a rotating magnetic field which drives the first magnet to rotate to drive the rotating shaft to rotate.

11. The drive device according to claim 10, wherein the drive stator comprises a plurality of first magnetic cores and a plurality of first coils respectively wound around the plurality of first magnetic cores, and the plurality of first magnetic cores are arranged at intervals around the axis of the rotating shaft for one circle.

12. The drive device according to claim 10, wherein the drive component further comprises a power stator fixedly connected to the drive housing, the power stator and the drive stator are arranged along the axis of the rotating shaft, the rotating shaft is capable of rotatably passing through the power stator, the magnetic assembly further comprises a second magnet, the second magnet is fixedly connected to the rotating shaft, the power stator is capable of generating a rotating magnetic field which drives the second magnet to rotate.

13. The drive device according to claim 12, wherein the magnetic assembly further comprises a flywheel fixedly connected to the rotating shaft, the flywheel is located between the power stator and the drive stator, and the first magnet and the second magnet are both arranged on the flywheel.

14. The drive device according to claim 13, wherein the flywheel comprises a disc-shaped portion, the rotating shaft fixedly passes through the disc-shaped portion, the first magnet and the second magnet are respectively arranged on opposite sides of the disc-shaped portion, the first magnet and the second magnet are ring-shaped Halbach array magnets, the first magnet comprises a plurality of first magnetic blocks with magnetization directions parallel to an axis of the first magnet, the second magnet comprises a plurality of second magnetic blocks with magnetization directions parallel to an axis of the second magnet, the plurality of second magnetic blocks and the plurality of first magnetic blocks are respectively arranged on the disc-shaped portion around the rotating shaft, each of the second magnetic blocks is arranged opposite to one of the first magnetic blocks in an extension direction of the rotating shaft, and the oppositely arranged first magnetic block and second magnetic block have opposite polarities at sides facing the disk-shaped portion.

15. The drive device according to claim 12, wherein the drive stator comprises a plurality of first magnetic cores and a first coil, and the plurality of first magnetic cores are arranged at intervals around the axis of the rotating shaft for one circle, the power stator comprises a plurality of second magnetic cores and a second coil, the plurality of second magnetic cores are arranged at intervals around the rotating shaft for one circle, the first magnetic core and the second magnetic core each comprise a magnetic pillar, the first coil is wound on the magnetic pillar of the first magnetic core, the second coil is wound on the magnetic pillar of the second magnetic core, a cross-sectional area of the magnetic pillar of the first magnetic core is greater than a cross-sectional area of the magnetic pillar of the second magnetic core.

16. The drive device according to claim 12, wherein the first magnet is located between the drive stator and the power stator, a protection portion is fixed inside the drive housing, a position of at least a portion of the protection portion corresponds to the position of the magnetic assembly, a protection gap is formed between the protection portion and an inner wall of the drive housing, the drive device further comprises an electric wire passing through the protection gap and electrically connected to the power stator, and the protection portion is located between the first magnet and the electric wire.

17. A blood pump, comprising a rotatable impeller and the drive device according to claim 1.

18. The blood pump according to claim 17, wherein the blood pump further comprises a cannula assembly fixedly connected to the drive device, the cannula assembly is provided with an outflow port, and the impeller is capable of rotatably being received in the cannula assembly, and wherein a position of the detection port corresponds to a position of the outflow port, or the position of the detection port is adjacent to the outflow port.

19. The blood pump according to claim 17, wherein the blood pump further comprises a catheter assembly fixedly connected to the drive housing, the catheter assembly is capable of passing perfusate into the drive housing, a gap for the perfusate to pass through is provided between the rotating shaft and the shaft sleeve assembly, and the probe is sealed in the receiving cavity.

* * * * *